United States Patent
Banks et al.

(10) Patent No.: US 11,672,493 B2
(45) Date of Patent: Jun. 13, 2023

(54) BREAST COMPRESSION PADDLE WITH ACCESS CORNERS

(71) Applicant: HOLOGIC, INC., Marlborough, MA (US)

(72) Inventors: Melissa Banks, Marlborough, MA (US); Mallory Berko, Marlborough, MA (US); Frank Cable, Marlborough, MA (US); Tarpit Patel, Marlborough, MA (US); Kenneth F. Defreitas, Marlborough, MA (US); Timothy R. Stango, Marlborough, MA (US)

(73) Assignee: Hologic, Inc., Marlborough, MA (US)

( * ) Notice: Subject to any disclaimer, the term of this patent is extended or adjusted under 35 U.S.C. 154(b) by 420 days.

(21) Appl. No.: 16/638,184

(22) PCT Filed: Aug. 10, 2018

(86) PCT No.: PCT/US2018/046312
§ 371 (c)(1),
(2) Date: Feb. 11, 2020

(87) PCT Pub. No.: WO2019/033029
PCT Pub. Date: Feb. 14, 2019

(65) Prior Publication Data
US 2020/0359975 A1 Nov. 19, 2020

Related U.S. Application Data

(60) Provisional application No. 62/544,615, filed on Aug. 11, 2017.

(51) Int. Cl.
*A61B 6/04* (2006.01)
*A61B 6/00* (2006.01)

(52) U.S. Cl.
CPC ............ *A61B 6/0414* (2013.01); *A61B 6/502* (2013.01)

(58) Field of Classification Search
CPC .. A61B 6/02; A61B 6/025; A61B 6/04; A61B 6/0407; A61B 6/0414;
(Continued)

(56) References Cited

U.S. PATENT DOCUMENTS

| 3,971,950 A | 7/1976 | Evans et al. |
| 4,496,557 A | 1/1985 | Malen |

(Continued)

FOREIGN PATENT DOCUMENTS

| AU | 2008201638 | 5/2008 |
| CN | 1586399 | 3/2005 |

(Continued)

OTHER PUBLICATIONS

European Extended Search Report in Application 18843788.3, dated Mar. 29, 2021, 16 pages.

(Continued)

*Primary Examiner* — Chih-Cheng Kao
(74) *Attorney, Agent, or Firm* — Merchant & Gould P.C.

(57) ABSTRACT

The present invention is directed to a breast compression paddle for a mammographic/tomosynthesis imaging system. The paddle including a front wall which is adjacent an imaged patient's chest. The bottom wall which is connected to a curved lower interface extends away from the chest wall and is adjacent to the top of a compressed breast. Two outer edges which extend away from the front reference surface, partially define a slightly raised central portion of the bottom wall. A bottom reference plane, a vertical reference plane substantially orthogonal to the front reference surface and the bottom reference plane, and an access surface disposed proximate at least one of the two outer edge portions are (Continued)

each defined by the bottom wall. The access surface is non-orthogonal to the front reference surface, the bottom reference plane, and the vertical reference plane.

19 Claims, 23 Drawing Sheets

(58) Field of Classification Search
CPC .......... A61B 6/0492; A61B 6/46; A61B 6/50; A61B 6/502; A61B 90/03; A61B 2090/033; A61B 2090/036; A61B 2560/04; A61B 2560/0406; A61B 2560/0425; A61B 2560/06
See application file for complete search history.

(56) References Cited

U.S. PATENT DOCUMENTS

| | | | |
|---|---|---|---|
| 4,943,986 A | 7/1990 | Barbarisi | |
| 5,051,904 A | 9/1991 | Griffith | |
| 5,107,255 A | 4/1992 | Shiraishi | |
| 5,199,056 A * | 3/1993 | Darrah | A61B 6/502 |
| | | | 378/208 |
| 5,359,637 A | 10/1994 | Webber | |
| 5,398,272 A | 3/1995 | Bouscary et al. | |
| 5,506,877 A | 4/1996 | Niklason | |
| 5,553,111 A | 9/1996 | Moore et al. | |
| D376,012 S | 11/1996 | Hixson, Sr. | |
| 5,706,327 A | 1/1998 | Adamkowski | |
| 6,289,235 B1 | 9/2001 | Webber | |
| 6,647,092 B2 | 11/2003 | Eberhard | |
| 7,123,684 B2 | 10/2006 | Jing et al. | |
| 7,203,348 B1 | 4/2007 | Karrsemeijer | |
| 7,245,694 B2 | 7/2007 | Jing et al. | |
| 7,430,272 B2 | 9/2008 | Jing et al. | |
| 7,583,786 B2 | 9/2009 | Jing et al. | |
| 7,831,296 B2 | 11/2010 | Defreitas | |
| 7,869,563 B2 | 1/2011 | Defreitas et al. | |
| 8,175,219 B2 | 5/2012 | DeFreitas et al. | |
| 8,787,522 B2 | 7/2014 | Smith et al. | |
| 9,050,009 B2 | 6/2015 | Den Heeten | |
| 9,226,718 B1 | 1/2016 | Baxley | |
| 9,332,947 B2 | 5/2016 | DeFreitas et al. | |
| 9,498,180 B2 | 11/2016 | Ren et al. | |
| 9,743,997 B2 | 8/2017 | Grimbergen | |
| 9,782,135 B2 | 10/2017 | Stango et al. | |
| 9,826,950 B2 | 11/2017 | Den Heeten | |
| 10,603,002 B2 | 3/2020 | Stango | |
| 2001/0038861 A1 | 11/2001 | Hsu | |
| 2002/0061090 A1 | 5/2002 | Lindstrom | |
| 2003/0007597 A1 | 1/2003 | Higgins et al. | |
| 2004/0066882 A1 | 4/2004 | Eberhard | |
| 2004/0066884 A1 | 4/2004 | Claus | |
| 2004/0066904 A1 | 4/2004 | Eberhard | |
| 2004/0218727 A1 | 11/2004 | Shoenfeld | |
| 2005/0008117 A1 | 1/2005 | Livingston | |
| 2005/0063509 A1 | 3/2005 | DeFreitas et al. | |
| 2005/0113681 A1 | 5/2005 | DeFreitas et al. | |
| 2005/0113683 A1 | 5/2005 | Lokhandwalla et al. | |
| 2006/0165215 A1 | 7/2006 | Galkin | |
| 2007/0223652 A1 | 9/2007 | Galkin | |
| 2007/0242794 A1 | 10/2007 | Stanton | |
| 2007/0280412 A1 | 12/2007 | Defreitas et al. | |
| 2008/0043904 A1 | 2/2008 | Hoernig | |
| 2008/0080668 A1 | 4/2008 | Kashiwagi | |
| 2008/0087830 A1 | 4/2008 | Kashiwagi | |
| 2008/0242979 A1 | 10/2008 | Fischer et al. | |
| 2009/0262887 A1 | 10/2009 | Iordache et al. | |
| 2009/0268865 A1 | 10/2009 | Ren | |
| 2009/0324049 A1 | 12/2009 | Kontos et al. | |
| 2010/0046698 A1 | 2/2010 | Lebovic et al. | |
| 2010/0049093 A1 | 2/2010 | Galkin | |
| 2010/0111249 A1 | 5/2010 | Mertelmeir et al. | |
| 2011/0058724 A1 | 3/2011 | Claus | |
| 2011/0087098 A1 | 4/2011 | Fischer et al. | |
| 2011/0257919 A1 | 10/2011 | Reiner | |
| 2012/0033868 A1 | 2/2012 | Ren | |
| 2012/0051522 A1 | 3/2012 | Nishino | |
| 2012/0114095 A1 | 5/2012 | Smith et al. | |
| 2012/0277625 A1 | 11/2012 | Nakayama | |
| 2013/0012837 A1 | 1/2013 | Krogure | |
| 2013/0028499 A1 | 1/2013 | Tsujii | |
| 2013/0272493 A1 | 10/2013 | Otokuni | |
| 2014/0107493 A1 | 4/2014 | Yuen | |
| 2014/0296701 A1 | 10/2014 | Hancu et al. | |
| 2014/0328458 A1 | 11/2014 | Erhard et al. | |
| 2014/0378816 A1 | 12/2014 | Oh | |
| 2015/0272682 A1 | 10/2015 | Sheng | |
| 2015/0282770 A1 | 10/2015 | Klanian et al. | |
| 2016/0066875 A1 | 3/2016 | Jacob et al. | |
| 2016/0081633 A1 * | 3/2016 | Stango | A61B 6/025 |
| | | | 378/37 |
| 2016/0183889 A1 | 6/2016 | Matsuura | |
| 2016/0242707 A1 | 8/2016 | Defreitas et al. | |
| 2017/0251991 A1 | 9/2017 | Wang | |
| 2017/0340303 A1 | 11/2017 | Stango | |
| 2018/0165840 A1 | 6/2018 | Bernard | |
| 2018/0184999 A1 * | 7/2018 | Davis | A61B 8/403 |
| 2020/0069274 A1 | 3/2020 | Stango | |
| 2020/0178926 A1 | 6/2020 | Kshirsagar | |
| 2020/0196971 A1 | 6/2020 | Laviola | |
| 2020/0359974 A1 | 11/2020 | DeFreitas | |
| 2020/0390405 A1 * | 12/2020 | Defreitas | A61B 6/04 |
| 2021/0015435 A1 * | 1/2021 | Defreitas | A61B 6/502 |
| 2021/0113169 A1 | 4/2021 | Stango | |
| 2021/0228165 A1 | 7/2021 | Defreitas | |
| 2022/0087627 A1 * | 3/2022 | Stango | A61B 6/025 |

FOREIGN PATENT DOCUMENTS

| | | |
|---|---|---|
| CN | 102196772 | 9/2011 |
| CN | 102448375 | 5/2012 |
| CN | 102781328 | 11/2012 |
| CN | 103281961 | 9/2013 |
| CN | 104066374 | 9/2014 |
| CN | 105286904 | 2/2016 |
| CN | 105637562 | 6/2016 |
| CN | 105769236 | 7/2016 |
| CN | 112004473 | 11/2020 |
| CN | 115348838 | 11/2022 |
| EP | 955886 | 11/1999 |
| EP | 2341832 A1 | 7/2011 |
| EP | 2943125 A1 | 11/2015 |
| JP | S53-103672 | 8/1978 |
| JP | H03-86154 | 4/1991 |
| JP | 2003-525681 | 9/2003 |
| JP | 2005-523043 | 8/2005 |
| JP | 2009-219656 | 10/2009 |
| JP | 8-215172 | 3/2010 |
| JP | 2011-072667 | 4/2011 |
| JP | 2011-206436 | 10/2011 |
| JP | 2011-224351 | 11/2011 |
| JP | 2011-250842 | 12/2011 |
| JP | 2012-125536 | 7/2012 |
| JP | 2012-170718 | 9/2012 |
| JP | 2012-228404 | 11/2012 |
| JP | 2013017491 | 1/2013 |
| JP | 2014-068884 | 4/2014 |
| JP | 2014-068885 | 4/2014 |
| JP | 2015-027382 | 2/2015 |
| JP | 2016-022061 | 2/2016 |
| JP | 2016-517740 | 6/2016 |
| KR | 10-2011-0089446 | 8/2011 |
| KR | 10-2014-0058066 A | 5/2014 |
| NL | 2020910 B1 | 11/2019 |
| WO | 2006/050466 | 5/2006 |
| WO | 2010/028208 | 3/2010 |
| WO | 2010/102087 A1 | 9/2010 |
| WO | 2011/058730 | 5/2011 |
| WO | 2014059366 | 4/2014 |
| WO | 2014/074602 | 5/2014 |
| WO | 2014/176445 | 10/2014 |
| WO | 2015/054518 | 4/2015 |
| WO | 2016/073445 | 5/2016 |

(56) References Cited

FOREIGN PATENT DOCUMENTS

| WO | 2018/067005 | 4/2018 |
|---|---|---|
| WO | 2018/089118 A1 | 5/2018 |
| WO | 2018/170265 | 9/2018 |
| WO | 2019/004821 | 1/2019 |
| WO | 2019/088826 | 5/2019 |
| WO | 20190227042 | 11/2019 |
| WO | 20190227044 | 11/2019 |

OTHER PUBLICATIONS

Digital Clinical Reports, Tomosynthesis (GE Brochure 98-5493, Nov. 1998), 8 pgs.

European Extended Search Report in Application 15857678.5, dated Jun. 26, 2018, 8 pages.

Grant, D.G., "Tomosynthesis: a three-dimensional imaging technique", IEEE Trans. Biomed. Engineering, vol. BME-19, #1, (Jan. 1972), pp. 20-28.

PCT International Preliminary Report on Patentability in International Application PCT/US2015/058782, dated May 18, 2017, 10 pgs.

PCT International Search Report and Written Opinion of the International Searching Authority for corresponding International Patent Application No. PCT/US2015/058782 dated Feb. 17, 2016, 14 pgs.

PCT International Search Report and Written Opinion of the International Searching Authority for International Patent Application No. PCT/US2017/053311 dated Mar. 6, 2018, 21 pages.

PCT International Search Report and Written Opinion of the International Searching Authority for International Patent Application No. PCT/US2018/046304 dated Dec. 11, 2018, 18 pages.

U.S. Appl. No. 60/628,516 entitled "Matching geometry generation and display of mammograms and tomosynthesis images", filed Nov. 15, 2004, 20 pgs.

PCT Invitation to Pay additional Fees, in Application PCT/US2021/013716, dated May 6, 2021, 17 pages.

PCT International Search Report and Written Opinion in International Application PCT/US2021/013716, dated Jun. 28, 2021, 24 pages.

European Communication and Search Report in Application 18847121.3, dated Apr. 8, 2021, 5 pages.

International Search Report and Written Opinion of the International Searching Authority for International Patent Application No. PCT/US2018/046312 dated Dec. 11, 2018, 14 pages.

European Extended Search Report in Application 18843590.3, dated Mar. 25, 2021, 9 pages.

Japanese Rejection in Application 2019-521374, dated Jul. 26, 2021, 5 pages.

PCT International Preliminary Reporton Patentability in International Application PCT/IB2018/056208, dated Feb. 27, 2020, 10 pages.

PCT International Search Report and Written Opinion in International Application PCT/IB2018/056208, dated Nov. 13, 2018, 12 pages.

PCT International Preliminary Report on Patentability in International Application PCT/US2017/053311, dated May 14, 2019, 13 pgs.

PCT International Preliminary Report on Patentability in International Application PCT/US2018/046304, dated Feb. 11, 2020, 13 pgs.

PCT International Preliminary Report on Patentability in International Application PCT/US2018/046312, dated Feb. 11, 2020, 11 pgs.

\* cited by examiner

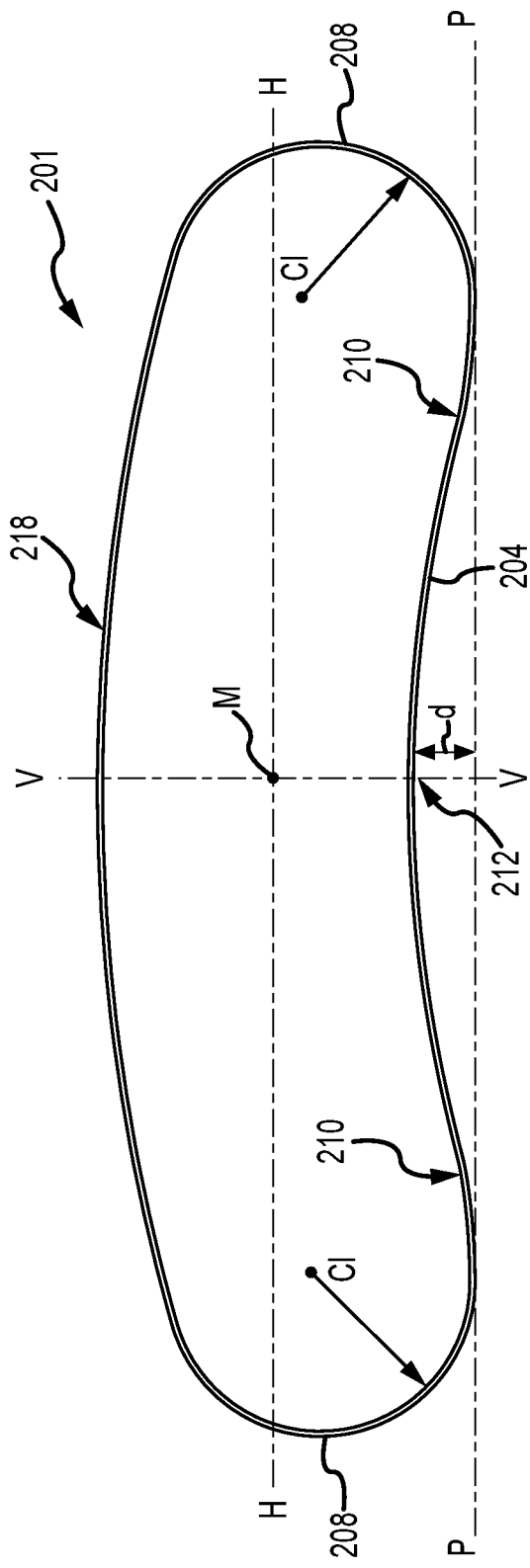
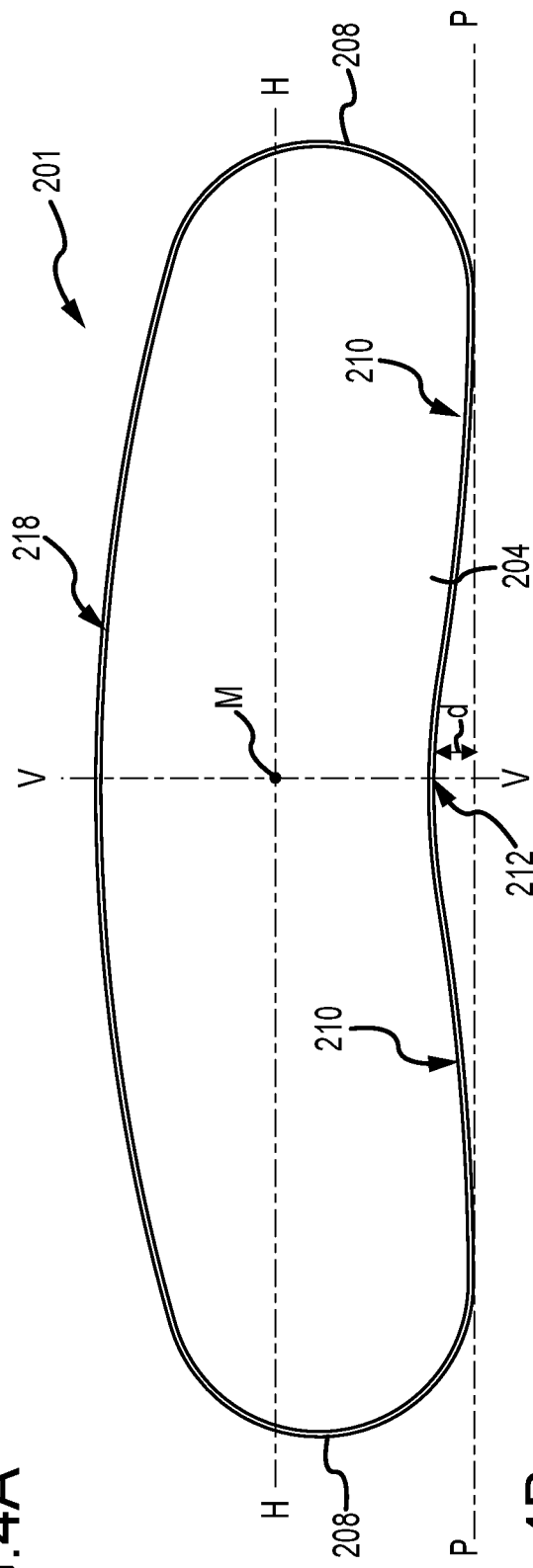
FIG.4A
FIG.4B

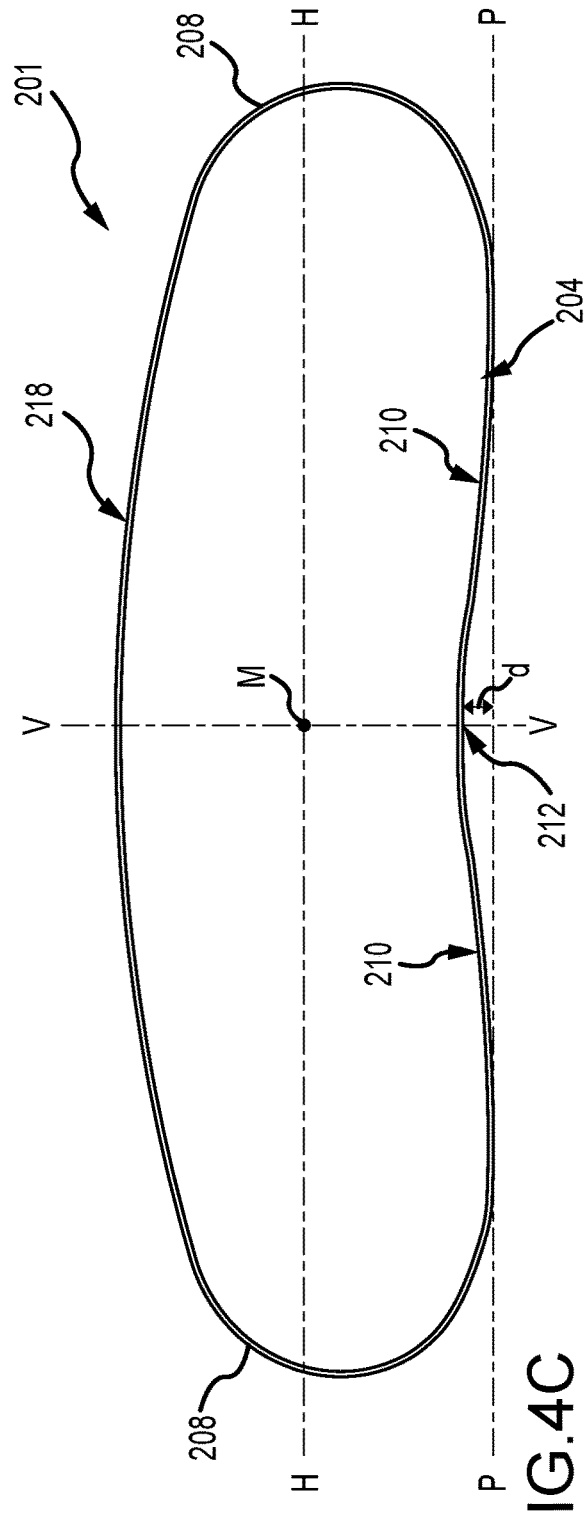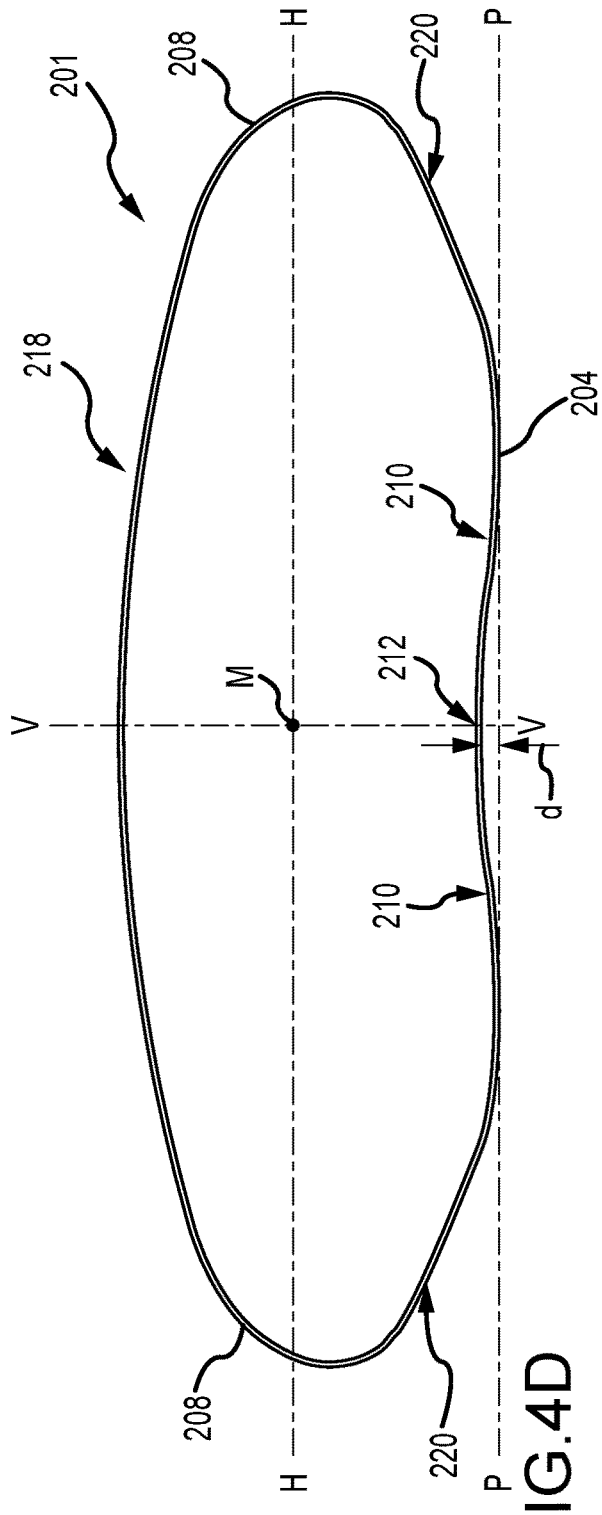

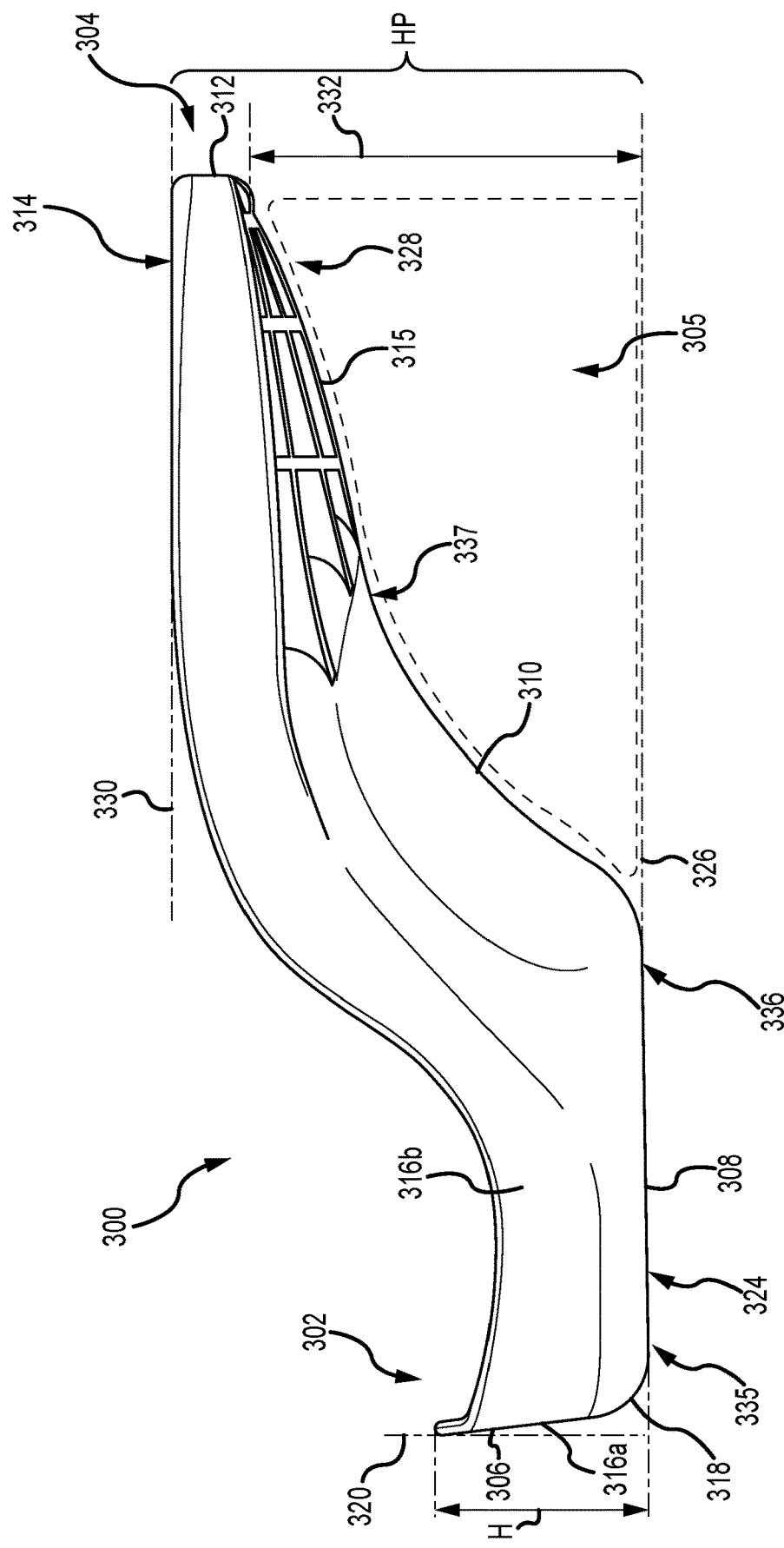

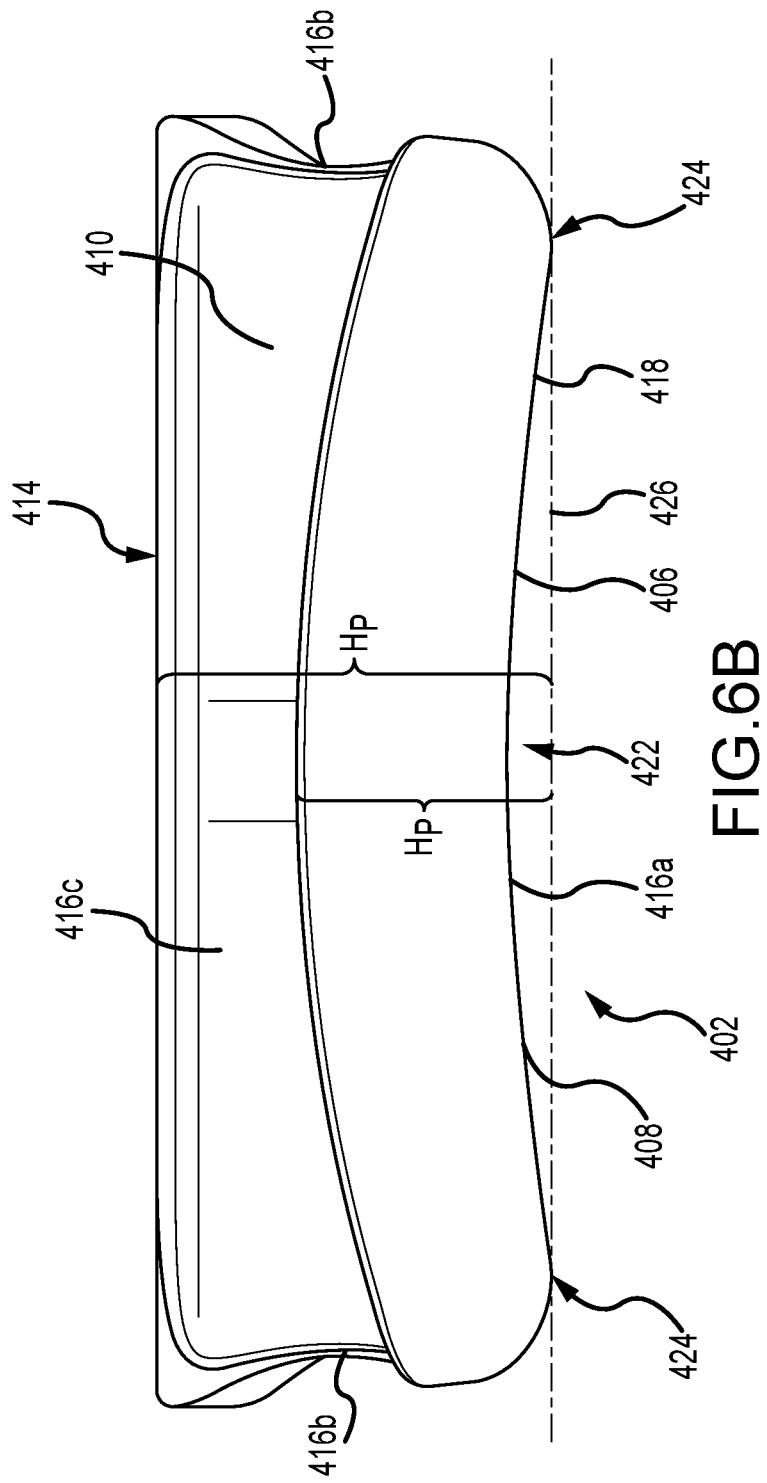

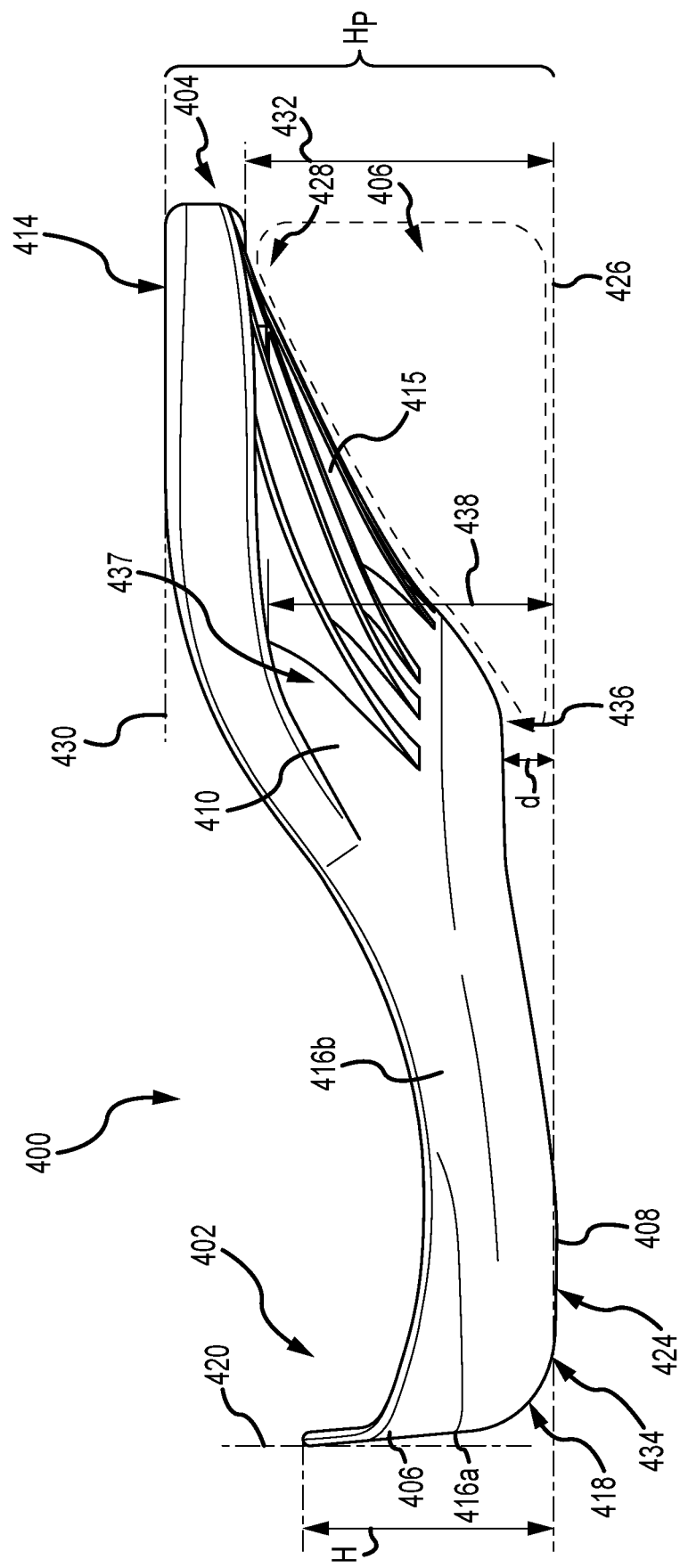

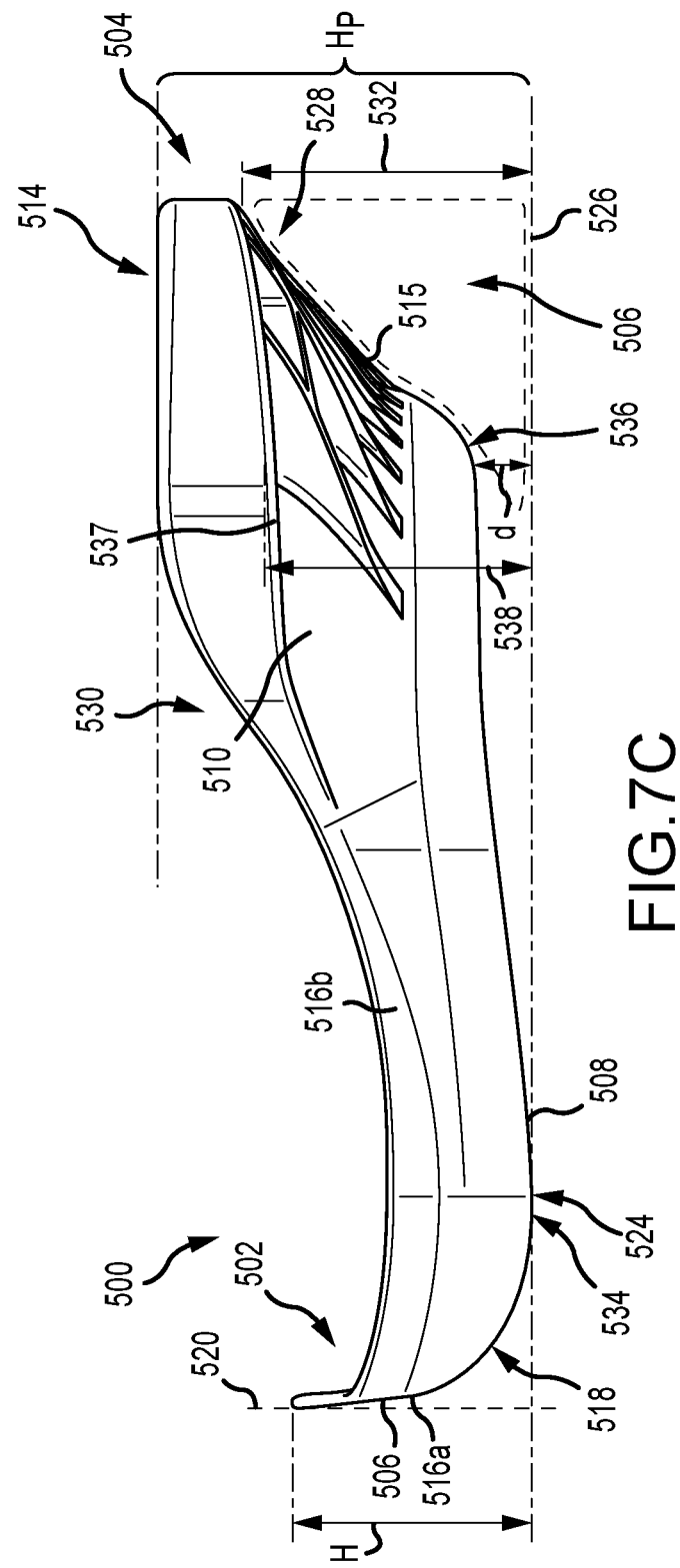

BREAST COMPRESSION PADDLE WITH ACCESS CORNERS

CROSS-REFERENCE TO RELATED APPLICATIONS

This application is being filed on 10 Aug. 2018, as a PCT International patent application, and claims priority to and the benefit of U.S. Provisional Patent Application Ser. No. 62/544,615, filed Aug. 11, 2017, entitled "Breast Compression Paddle with Access Corners," the disclosure of which is hereby incorporated by reference herein in its entirety.

INTRODUCTION

A significant concern in x-ray mammography and breast tomosynthesis is the discomfort the patient may feel when the breast is compressed, typically, between two rigid plastic surfaces, with sufficient force to immobilize the breast and spread out the breast tissues for x-ray imaging. One challenge is to ensure that the imaged field includes the desired amount of breast tissue. The reasons for using compression include: (1) to make the breast thinner in the direction of x-ray flux and thereby reduce patient radiation exposure from the level required to image the thicker parts of a breast that is not compressed; (2) to make the breast more uniform in thickness in the direction of x-ray flux and thereby facilitate more uniform exposure at the image plane over the entire breast image; (3) to immobilize the breast during the x-ray exposure and thereby reduce image blurring; and (4) to bring breast tissues out from the chest wall into the imaging exposure field and thus image more tissue. As the breast is being compressed, typically a technician manipulates the breast to position it appropriately and counter the tendency that compression has of pushing breast tissue toward the chest wall and out of the image field.

Standard compression methods for mammography and tomosynthesis use a movable, rigid clear plastic compression paddle in which the surfaces of the paddle are perpendicular to one another. The breast is placed on a breast platform that typically is flat, and the paddle is then compressed onto the breast, usually while a technician or other health professional is holding the breast in place and perhaps manipulates the breast to ensure proper tissue coverage in the image receptor's field of view and to help spread the breast. However, the size and shape of the paddle often prevent the technician from properly holding and manipulating the breast. That is, the technician's hand may get stuck between the compression paddle and breast as it is lowered, which can cause stress to both the patient and the technician. Alternatively, the technician may release the breast too soon in an effort to avoid getting stuck, resulting in undesirable compression. Both circumstances may potentially increase the length of the procedure, adversely impact patient positioning, and affect image quality

SUMMARY

In one aspect, the technology relates to a breast compression paddle for an imaging system, the breast compression paddle having: a front wall configured to be adjacent and face a chest wall of a patient during imaging, wherein the front wall has a front reference surface adjacent the chest wall; a bottom wall connected to the curved lower interface and configured to extend away from the chest wall and to be adjacent a length of a top of a compressed breast, wherein the bottom wall has a central portion and two outer edge portions at least partially defining the central portion, wherein the central portion is raised relative to the two outer edge portions, and wherein the two outer edge portions extend away from the front reference surface, and wherein the bottom wall defines a bottom reference plane; a vertical reference plane substantially orthogonal to each of the front reference surface and the bottom reference plane; and an access surface disposed proximate at least one of the two outer edge portions, wherein the access surface is non-orthogonal to each of the front reference surface, the bottom reference plane, and the vertical reference plane. In an example, the front wall has a curved interface having an upper extent, and wherein the front reference surface extends tangential to the upper extent. In another example, the access surface has two access surfaces, wherein one access surface is disposed proximate each of the two outer edge portions. In yet another example, each of the two outer edge portions define a contour line having a linear portion and a curved portion. In still another example, the each access surface intersects one of the two outer edge portions proximate the curved portion.

In another example of the above aspect, a height of the central portion over the bottom reference plane decreases as a distance away from the front wall increases. In an example, the breast compression paddle has a curved top surface.

In another aspect, the technology relates to an imaging system having: a breast platform configured to support a breast of a patient, the breast platform defining a top horizontal surface and a forward surface configured to be adjacent to a chest wall of the patient when the breast is supported by the breast platform; a vertical reference plane disposed orthogonal to the breast platform and the forward surface; a horizontal reference plane disposed a predetermined distance above the breast platform and parallel to the breast platform; an x-ray source disposed above the horizontal reference plane; and a compression paddle disposed between the breast platform and the x-ray source for compressing the breast against the platform, the compression paddle having: a front wall configured to be adjacent to the chest wall of the patient when the breast is supported by the breast platform, wherein the horizontal reference plane is disposed at a horizontal midpoint of the front wall and a vertical midpoint of the front wall; a bottom wall configured to be adjacent to the breast of the patient when the breast is supported by the breast platform; a front cross section defined by the bottom wall and the horizontal reference plane, the front cross section disposed orthogonal to the horizontal reference plane proximate the front wall; and a rear cross section defined by the bottom wall and the horizontal reference plane, the rear cross section disposed a predetermined distance from the front wall, wherein the front cross section is different than the rear cross section. In an example, a portion of the bottom wall intersecting the vertical reference plane is disposed a first distance below the horizontal reference plane at the front cross section and a second distance below the horizontal reference place at the rear cross section, wherein the first distance is less than the second distance. In another example, the imaging system includes two outer edge portions at least partially defining the bottom wall, wherein the two outer edge portions are disposed a first distance from the vertical reference plane at the first cross section and a second distance from the vertical reference plane at the rear cross section, wherein the first distance is greater than the second distance. In yet another example, the outer edge portions have a substantially linear portion and a substantially curved portion. In still another example, the first cross section includes outer contours defined by a first boundary and wherein the second cross section includes outer contours defined by a second boundary different than the first boundary.

In another aspect, the technology relates to an imaging system having: a breast platform configured to support a breast of a patient, the breast platform defining a top horizontal surface and a forward surface configured to be adjacent to a chest wall of the patient when the breast is supported by the breast platform; a vertical reference plane disposed orthogonal to the breast platform and the forward surface; a horizontal reference plane disposed a predetermined distance above the breast platform and parallel to the breast platform; an x-ray source disposed above the horizontal reference plane; and a compression paddle disposed between the breast platform and the x-ray source for compressing the breast against the platform, the compression paddle having: a front wall configured to be adjacent to the chest wall of the patient when the breast is supported by the breast platform, wherein the horizontal reference plane is disposed at a horizontal midpoint of the front wall and a vertical midpoint of the front wall; a bottom wall configured to be adjacent to the breast of the patient when the breast is supported by the breast platform, wherein the bottom wall has a contact surface, wherein the contact surface is defined at least in part by two outer edge portions; and a plurality of cross sections defined by the bottom wall and the horizontal reference plane, wherein the plurality of cross sections are disposed orthogonal to the horizontal reference plane, wherein a distance between the vertical reference plane and the two outer edge portions decreases as a cross section distance from the front wall increases. In an example, a distance of the contact surface below the reference plane increases as the cross section distance from the front wall increases. In another example, the plurality of cross sections include outer contours that change in shape as the cross section distance from the front wall increases. In yet another example, the plurality of outer contours change from a curved shape to a substantially linear shape as the cross section distance from the front wall increases. In still another example, the plurality of outer contours include a width that varies as the cross section distance from the wall increases. In another example of the above aspect, the width decreases as the cross section distance from the wall increases. In an example, the compression paddle has a top wall. In another example, the top wall is curved. In another example, the top wall is curved.

In another aspect, the technology relates to a breast compression paddle for an imaging system, the breast compression paddle having: a front wall configured to be adjacent and face a chest wall of a patient during imaging, wherein the front wall includes a front wall height, a curved lower interface, and a front reference plane adjacent the chest wall; a bottom wall connected to the curved lower interface and configured to extend away from the chest wall and to be adjacent a length of a top of a compressed breast, wherein the bottom wall includes a central portion and two outer edge portions at least partially defining the central portion, and wherein the two outer edge portions extend away from the front reference plane, and wherein the two outer edge portions define a bottom reference plane; and a bracket distal from the front wall, wherein the bracket includes a paddle top surface and a bracket underside surface, and wherein the paddle top surface includes a top reference plane disposed a maximum paddle height above the bottom reference plane, and wherein the maximum paddle height is greater than the front wall height. In an example, the bracket includes a rear bracket wall disposed opposite the front wall and connecting the paddle top surface and the bracket underside surface, and wherein the rear bracket wall terminates at a distance above the bottom reference plane greater than the front wall height. In another example, the bracket underside surface includes a portion of the paddle disposed directly below the paddle top surface that defines the top reference plane. In yet another example, the breast compression paddle further having a plurality of ribs disposed below the paddle top surface. In still another example, the breast compression paddle further having a transition wall connecting the bracket underside surface and the bottom wall.

In another example of the above aspect, the bottom wall and the transition wall are substantially surrounded by a perimeter wall extending upward towards the top reference plane, wherein the bottom wall, the transition wall, and the perimeter wall define a semi-bounded volume. In an example, the bottom wall and the transition wall include a lower surface of the semi-bounded volume, and wherein a portion of the lower surface proximate the bottom wall is non-concave. In another example, a portion of the lower surface proximate the transition wall is substantially concave. In yet another example, a portion of the lower surface proximate the transition wall is substantially convex. In still another example, the front wall includes an indentation disposed at an angle to the front wall.

In another aspect, the technology relates to a breast compression paddle for an imaging system, the breast compression paddle having: a plurality of boundary walls having a front boundary wall, a rear boundary wall, and two lateral boundary walls extending from the front boundary wall to the rear boundary wall; a bracket portion extending from the rear boundary wall away from the front boundary wall; and a bottom wall connected to each of the plurality of boundary walls at a curved interface, wherein the bottom wall includes at least three points defining a bottom reference plane, and wherein an uppermost portion of the front boundary wall is disposed at a front boundary wall height above the bottom reference plane, and wherein an uppermost portion of the rear boundary wall is disposed at a rear boundary wall height above the bottom reference plane, and wherein the front boundary wall height is less than the rear boundary wall height. In an example, the bottom wall includes a raised central portion and a plurality of outer edge portions, and wherein the at least three points are disposed on the plurality of outer edge portions. In another example, the bottom wall includes two outer edge portions disposed proximate the two lateral boundary walls, and a central portion substantially level with the two outer edge portions. In yet another example, the bottom wall includes a proximate portion disposed proximate to the front boundary wall and a distal portion disposed distal from the front boundary wall and wherein the distal portion is disposed a distal portion distance above the bottom reference plane. In still another example, the bracket portion is connected to the rear boundary wall and includes a rear paddle wall disposed opposite from the rear boundary wall and disposed substantially parallel to the rear boundary wall.

In another example of the above aspect, the breast compression paddle further having a plurality of ribs spanning from the rear boundary wall to the rear paddle wall. In an example, at least one of the plurality of ribs contacts at least a portion of the bottom wall. In another example, at least a bottom wall includes a transition wall, wherein at least a portion of the transition wall is convex. In yet another example, the front boundary wall defines a recess having an upper width disposed proximate the uppermost portion of the front boundary wall and a lower width disposed proximate the bottom wall, wherein the lower width is greater than the upper width. In still another example, the recess is disposed at an angle to the front boundary wall.

In another aspect, the technology relates to a breast compression paddle having: a bottom wall having a patient contact surface and a patient access surface, wherein during a compression of the breast, the patient contact surface is in contact with the breast and the patient access surface is disposed a distance from the patient contact surface so as to not contact the breast; a transition wall between and connecting the patient contact surface and the patient access surface, wherein the transition wall is a generally smooth curvature; a front wall, wherein during a compression of the breast, the front wall is in contact with the chest wall; and an interface wall between and connecting the patient contact surface and the front wall, wherein the interface wall is a generally smooth curvature.

This summary is provided to introduce a selection of concepts in a simplified form that are further described below in the Detailed Description. This summary is not intended to identify key features or essential features of the claimed subject matter, nor is it intended to be used to limit the scope of the claimed subject matter.

BRIEF DESCRIPTION OF THE DRAWINGS

The same number represents the same element or same type of element in all drawings.

FIGS. 4A-4E are cross sectional views of the compression paddle of FIG. 3E.

FIGS. 5A-5C are perspective, front, and side views, respectively, of another example of a compression paddle.

FIGS. 6A-6C are perspective, front, and side views, respectively, of another example of a compression paddle.

FIGS. 7A-7C are perspective, front, and side views, respectively, of another example of a compression paddle.

DETAILED DESCRIPTION

Figure 1:
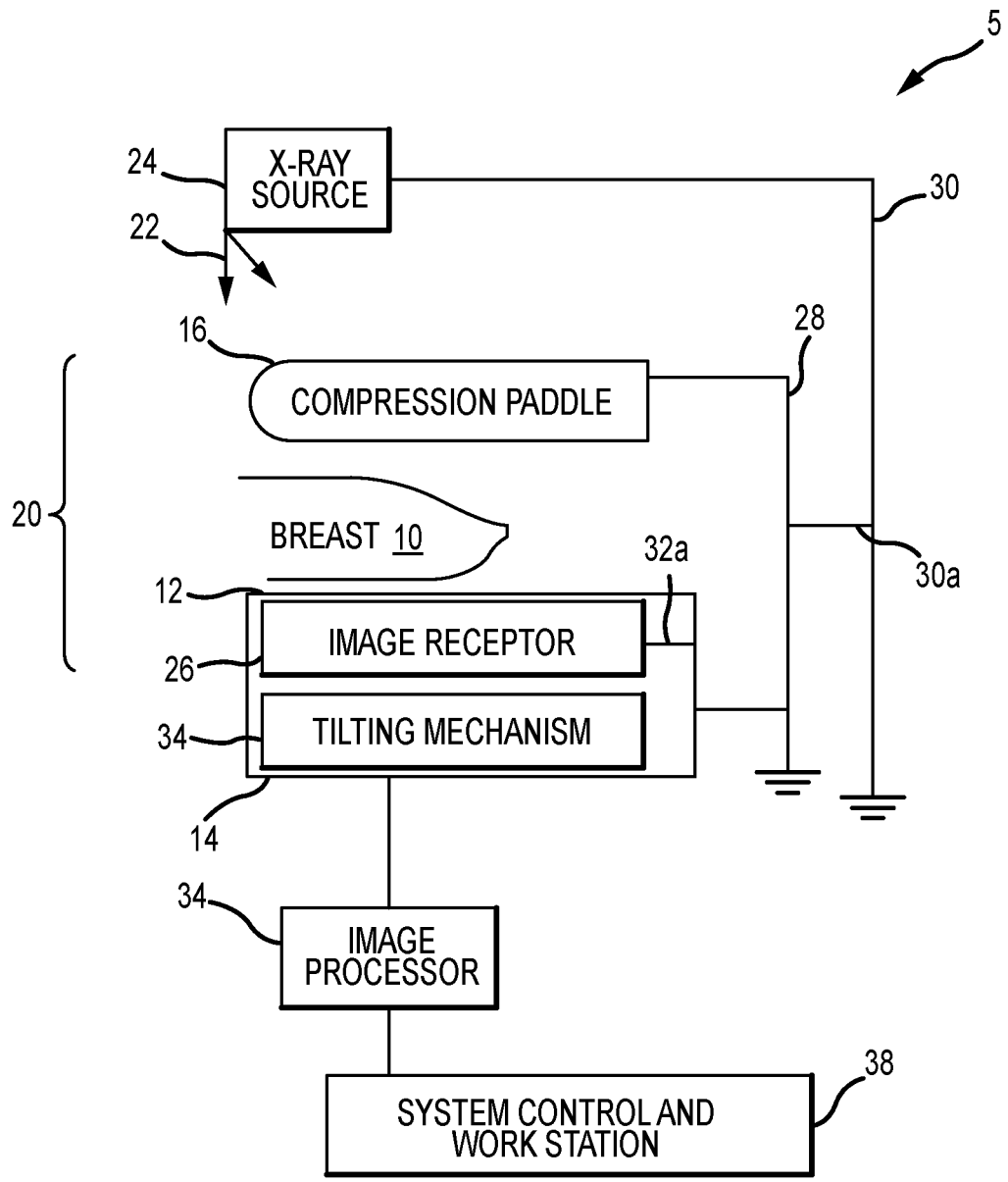
FIG. 1 is a schematic view of a mammography and/or tomosynthesis system.
Figure 2:
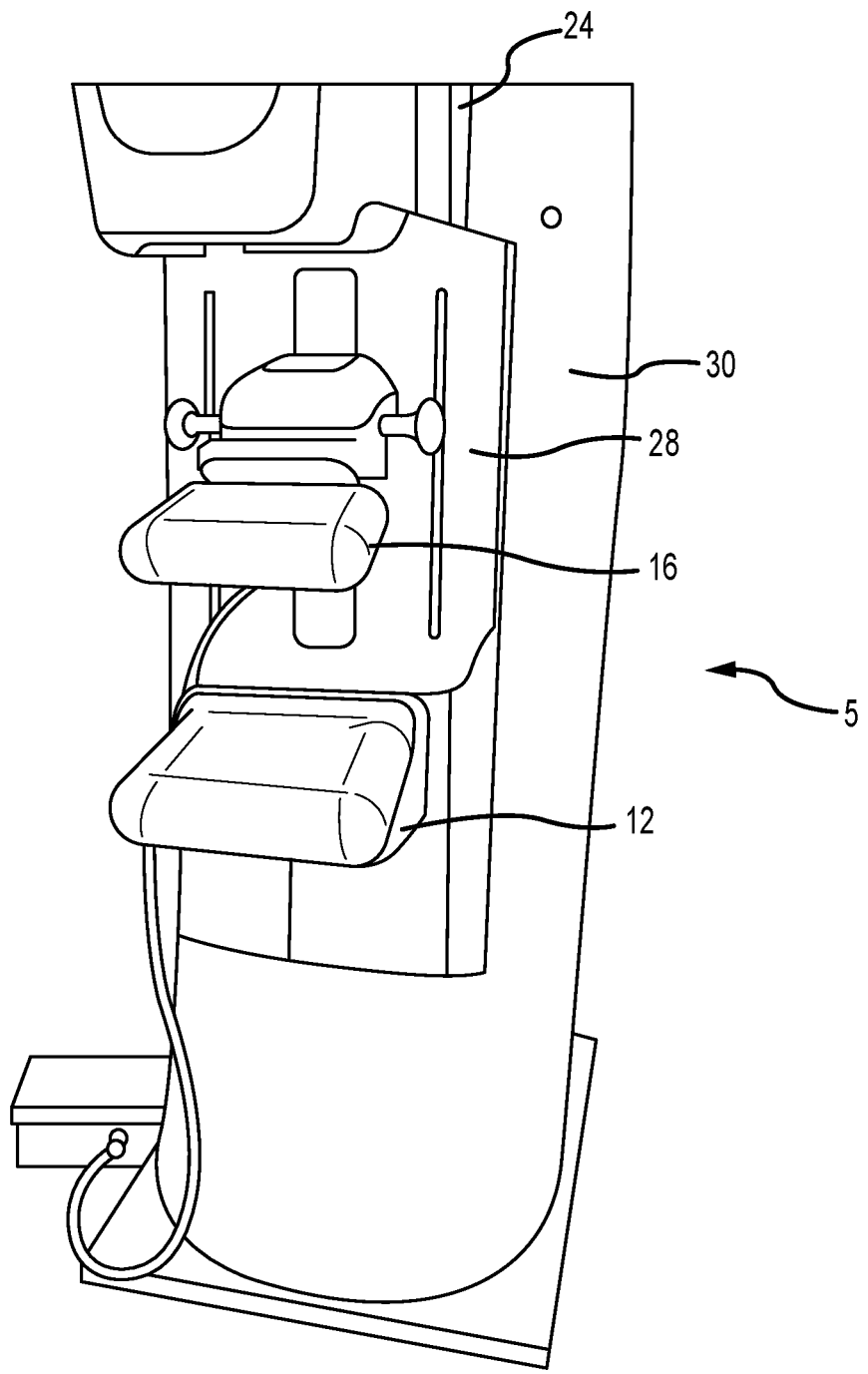
FIG. 2 is a partial perspective view of a mammography and/or tomosynthesis system.

FIG. 1 is a schematic view of a mammography and/or tomosynthesis system 5 using a compression paddle in imaging a patient's breast with x-rays. FIG. 2 illustrates in perspective view a system 5 in which components are identified by reference numeral used in FIG. 1 and described in concurrently with FIG. 1. A patient's breast 10 is immobilized for x-ray imaging between a breast platform 12 and a compression paddle 16. Platform 12 can be the upper surface of a housing 14. Platform 12 and paddle 16 form a breast immobilizer unit 20 that is in a path of an imaging beam 22 emanating from x-ray source 24. Beam 22 impinges on image receptor 26 that is in housing 14.

Immobilizer 20 and housing 14 are supported on an arm 28. X-ray source 24 is supported on an arm 30. For mammography, support arms 28 and 30 can rotate as a unit about an axis such as at 30a between different imaging orientations such as CC and MLO, so that the system 5 can take a mammogram projection image Mp at each orientation. Image receptor 26 remains in place relative to housing 14 while an image Mp is taken. Immobilizer 20 releases breast 10 for movement of arms 28 and 30 to a different imaging orientation. For tomosynthesis, support arm 28 stays in place, with breast 10 immobilized and remaining in place, while at least source support arm 30 rotates source 24 relative to immobilizer 20 and breast 10 about an axis such as 30a.

The system takes plural tomosynthesis projection images of breast 10 at respective angles of beam 22 relative to breast 10. Concurrently, image receptor 26 may be tilted relative to breast platform 12 in sync with the rotation of source support arm 30. The tilting can be through the same angle as the rotation of course 24, but preferably is through a different angle, selected such that beam 22 remains substantially in the same position on image receptor 26 for each of the plural images Tp. The tilting can be about an axis 32a, which can but need not be in the image plane of image receptor 26.

In one embodiment, optionally, a tilting mechanism 34, which also is in housing 14 or is otherwise coupled with receptor 24, can drive image receptor 24 in a tilting motion. Axes 30a and 32a extend left-right as seen in FIG. 1, and may but preferably do not coincide. For tomosynthesis imaging, breast platform 12 can be horizontal or can be at an angle to the horizontal, e.g., at an orientation similar to that for conventional MLO imaging in mammography. The system of FIG. 1 can be solely a mammography system, or solely a tomosynthesis system, or a "combo" system that can perform both mammography and tomosynthesis imaging. An example of such a combo system is been offered by the assignee hereof under the trade name Selenia Dimensions. Nonlimiting examples of such a combo system or a tomosynthesis system are described at U.S. Pat. Nos. 7,869,563; 7,831,296; 7,583,786; 7,430,272; 7,245,694; and 7,123,684. When the system is operated, image receptor 26 produces imaging information in response to illumination by imaging beam 22, and supplies it to image processor 34 for processing to generate breast x-ray images. Given the complex shapes of the compression paddles described herein, the image processor may utilize image processing functionality as described in co-owned PCT Publication No. WO 2018/089118, filed Sep. 25, 2017, entitled "Imaging with Curved Compression Elements," the disclosure of which is hereby incorporated by reference herein in its entirety. A system control and work station unit 38 controls the operation of the system and interacts with a user to receive commands and deliver information including processed-ray images.

Figure 3:
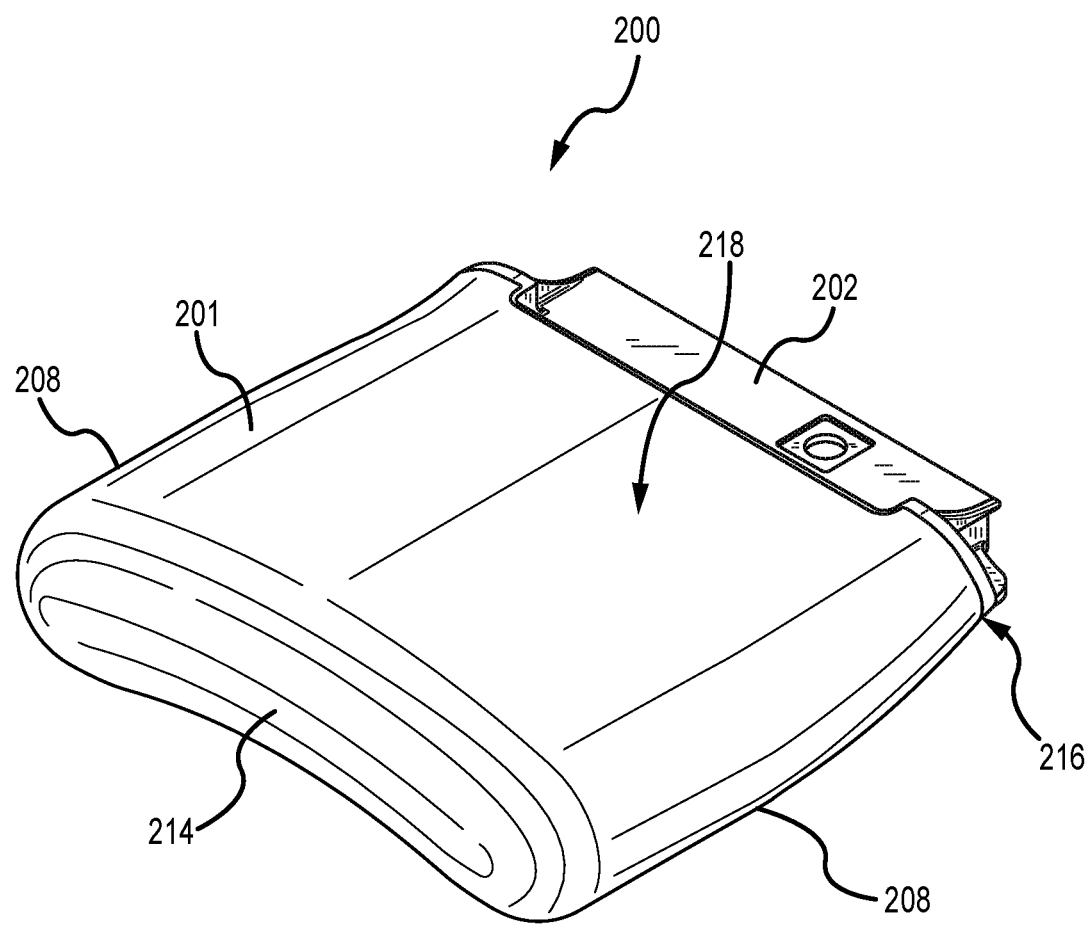
FIG. 3 is an upper perspective view of a compression paddle and bracket.
Figure 3A:
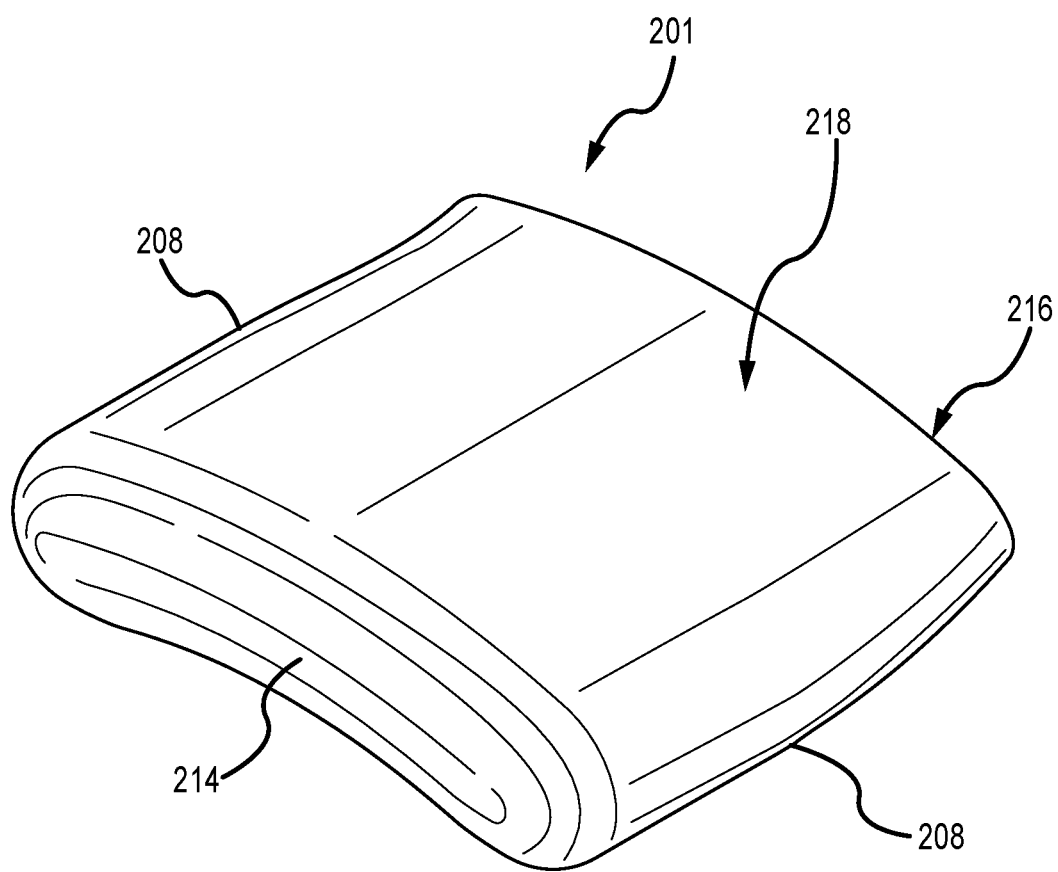
FIGS. 3A and 3B are upper and lower perspective views of a compression paddle.
Figure 3B:
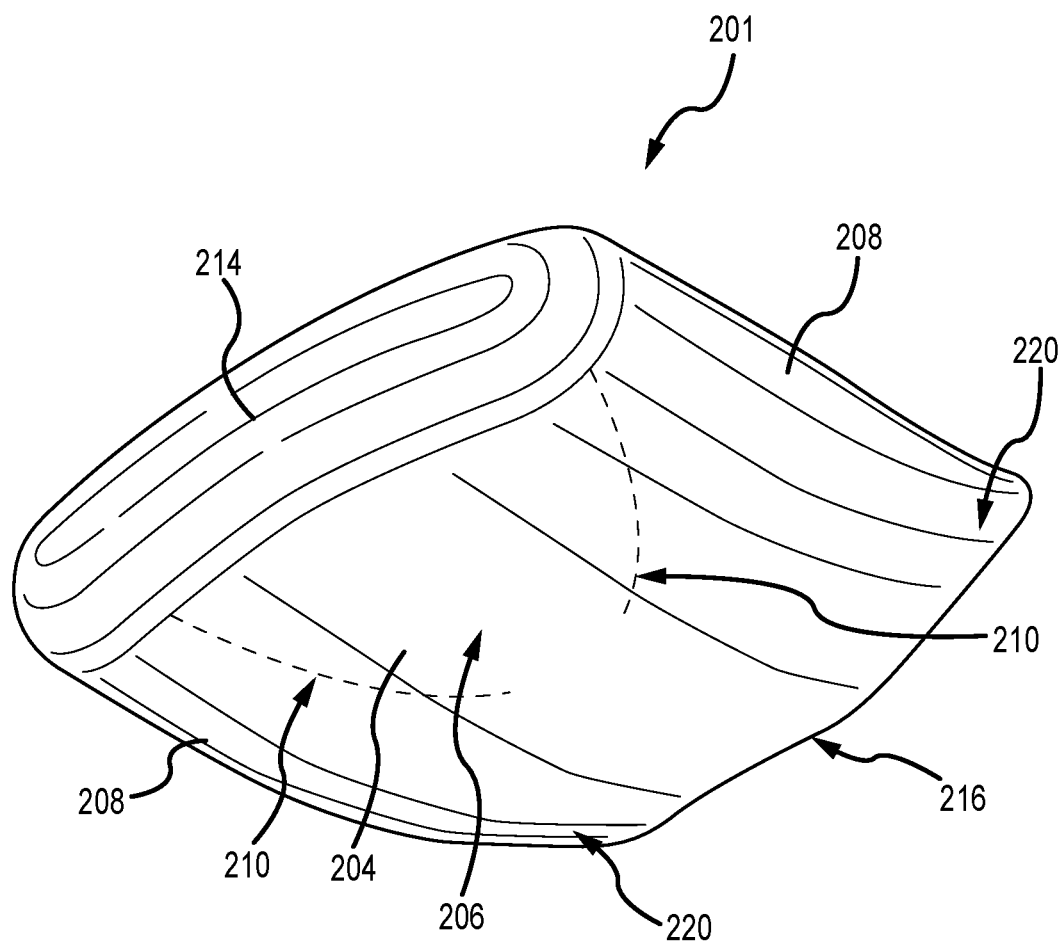
Figure 3C:
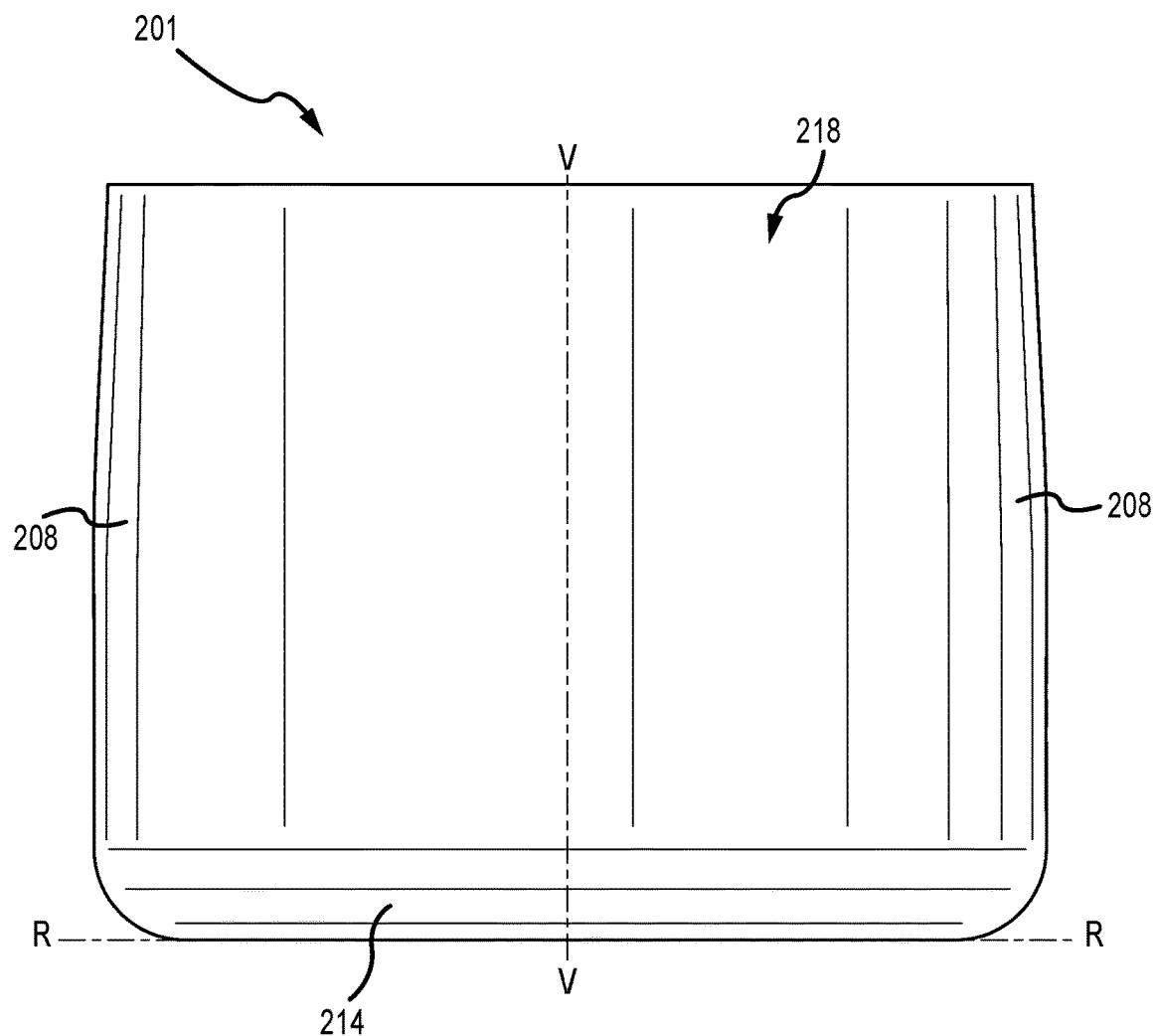
FIGS. 3C-3H are various views of the compression paddle of FIGS. 3A and 3B.
Figure 3D:
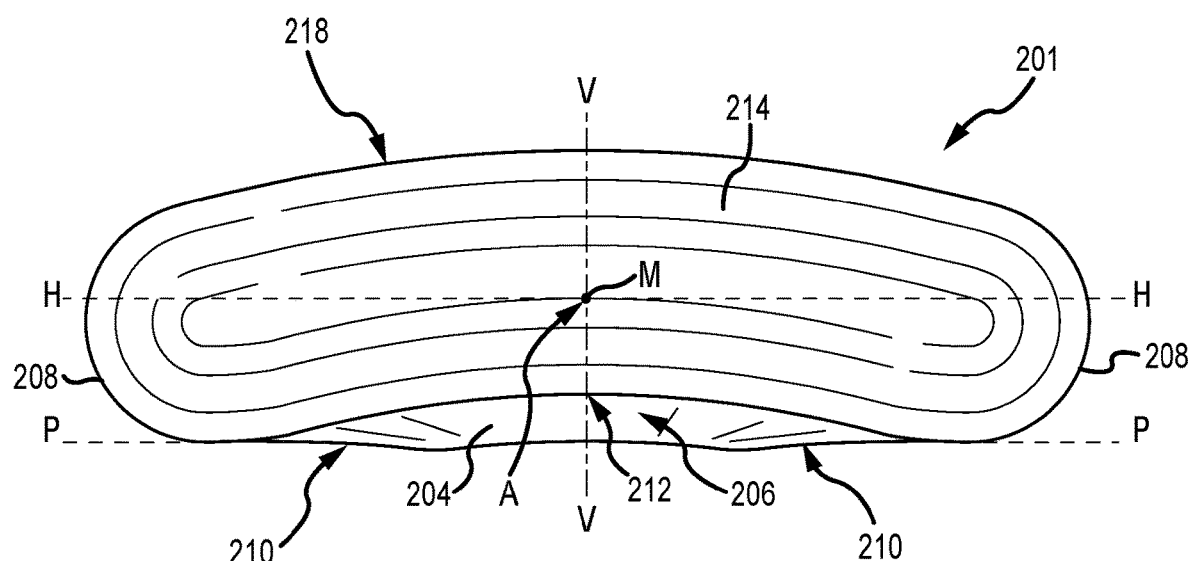
Figure 3E:
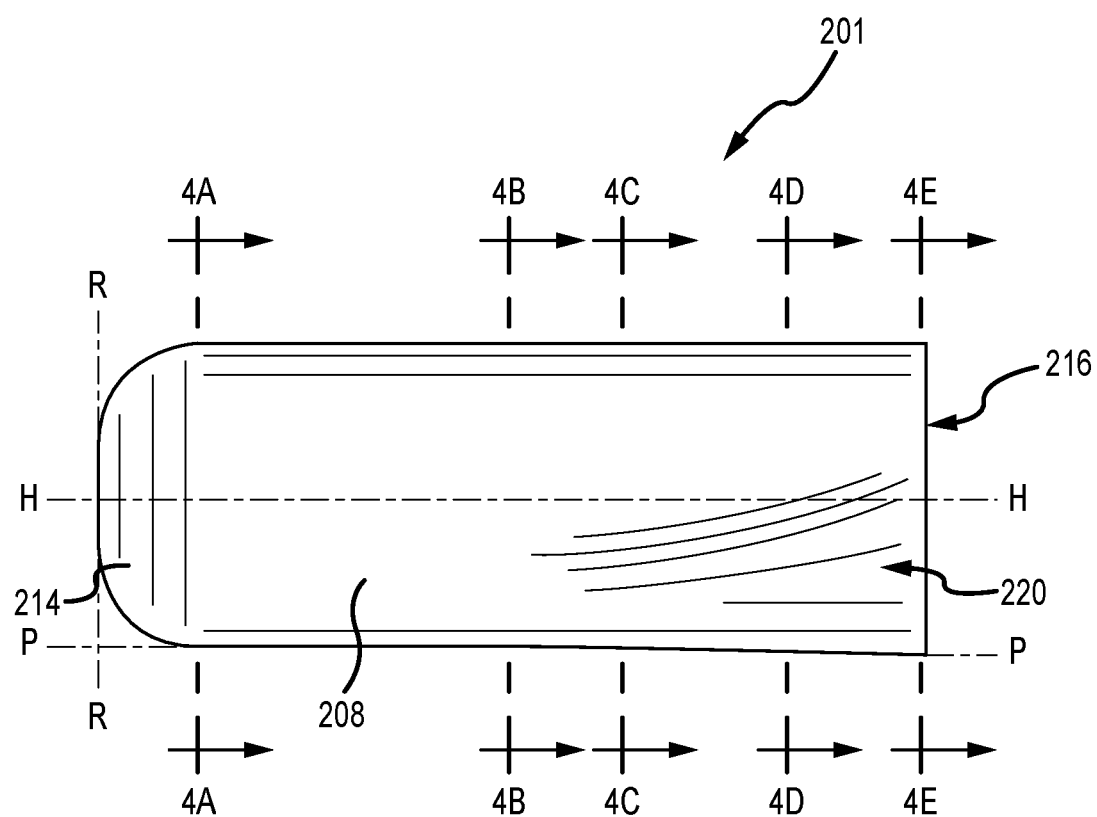
Figure 3F:
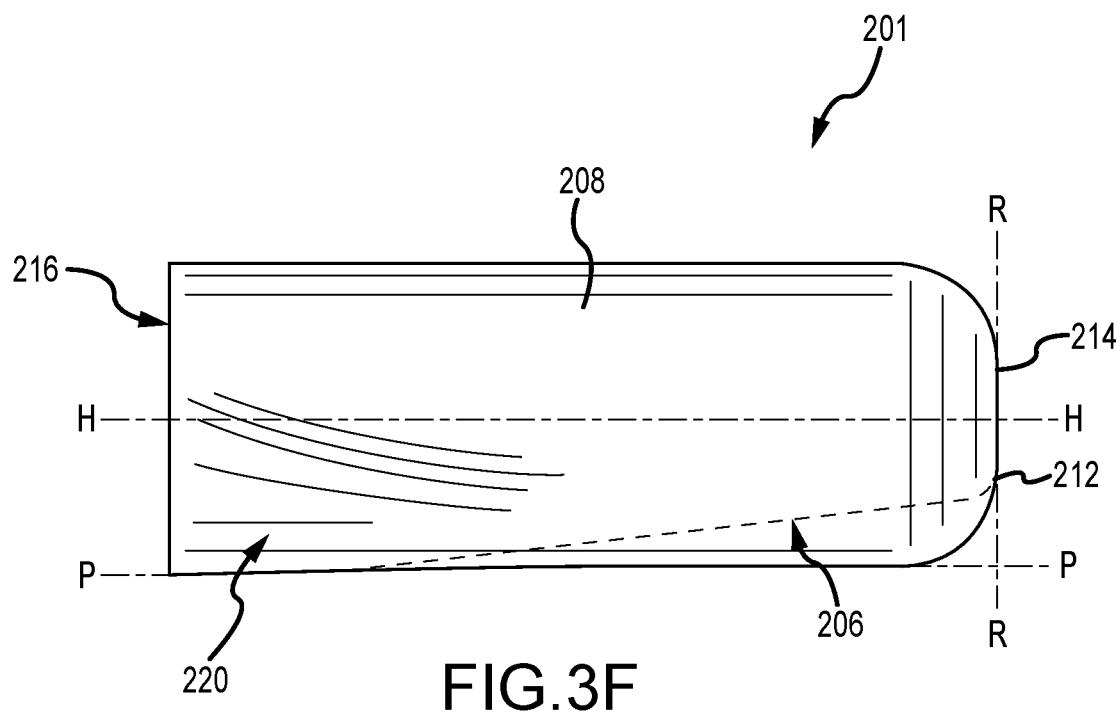
Figure 3G:
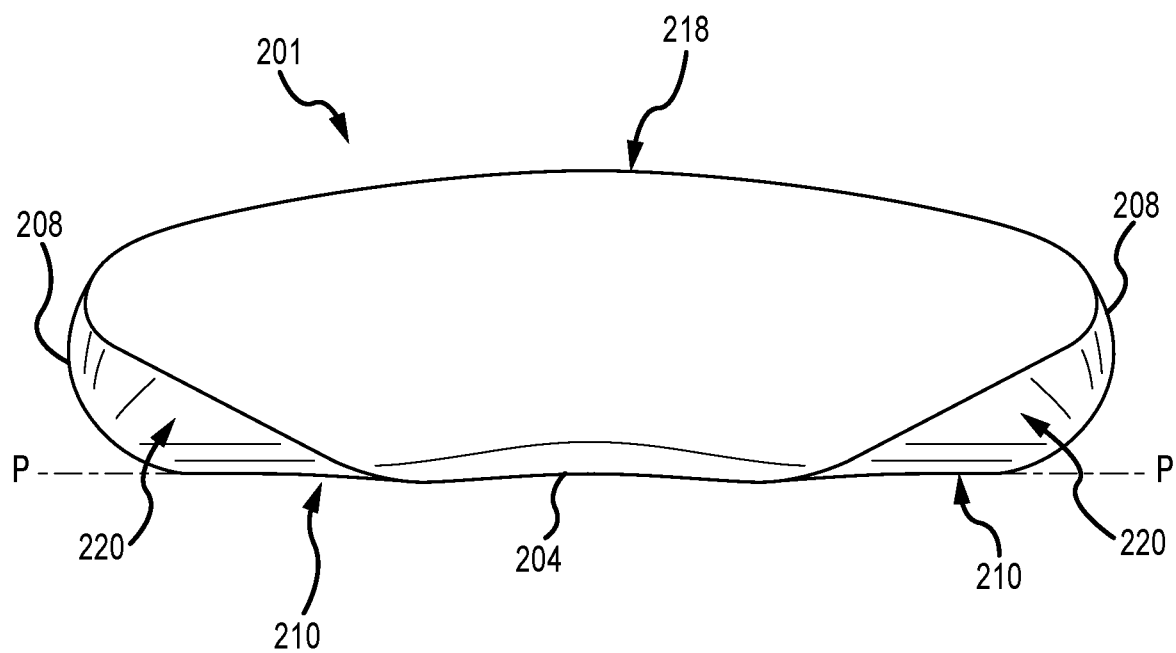
Figure 3H:
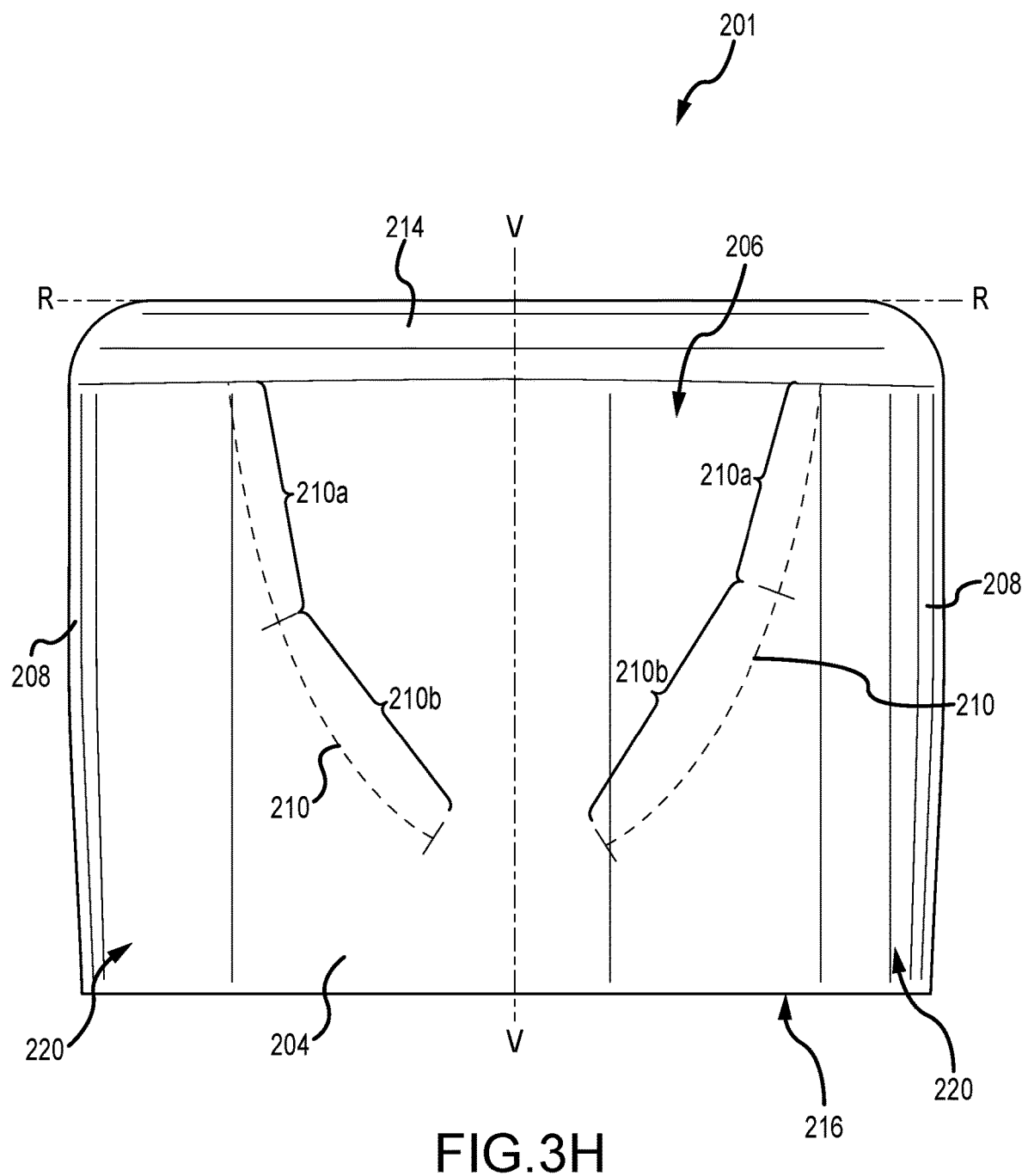

FIG. 3 is an upper perspective view of a compression element 200 including a compression paddle 201 and bracket 202, while FIGS. 3A and 3B are upper and lower perspective views of the compression paddle 201. FIGS. 3C-3H are various views of the compression paddle 201 of FIGS. 3A and 3B. FIGS. 3-3H are described concurrently. The compression paddle 201 compresses a breast of a patient during imaging procedures. The bracket 202 removably connects the compression element 200 to an arm of the imaging system. The depicted compression paddle 201 is configured to allow a technician to have improved access to a patient breast during lowering of the compression paddle 201. This operation is described in more detail below. The compression paddle 201 includes a number of features that enable such access.

A bottom wall 204 of the compression paddle 201 includes a generally concave surface 206, which generally may correspond in shape to a breast and/or a compressed breast. The generally concave surface 206 can extend generally between the rounded side walls 208 of the compression paddle 201. Alternatively, only a portion of the bottom surface includes a generally concave surface, which helps to match the contour of breast tissue. The generally concave surface 206 helps to distribute more equally forces applied to the breast to more closely correspond to the shape of the breast. Such a configuration may help provide more comfort to a patient as the breast is being compressed. The generally concave surface 206 is defined by an outer edge 210 (depicted by dashed lines in FIGS. 3B and 3H) that defines a bottom reference plane P, as well as a central portion 212. In another example, the lowest part of the compression paddle 201 (that is, the portions on which the compression paddle 201 may rest when placed on a flat surface) may define the bottom reference plane P. In the depicted example, the shape of the outer edge 210 changes as distance from a front wall 214 of the compression paddle 201 increases. As can be seen, proximate the front wall 214, the outer edges 210 are more linear 210a in configuration, while further therefrom, the shape is more curved 210b. In another example, the outer edges 210 may be linear in configuration along their entire lengths. This is to mimic the approximate outer shape of a breast. The central portion 212 is non-coplanar with the outer edge 210, such that the central portion 212 is raised relative to or disposed above the bottom reference plane P. The central portion 212 may be level (e.g., parallel to the bottom reference plane P of the paddle 201) or may be pitched downward from the rounded front wall 214 to a rear edge 216 (where the paddle 201 connects to the bracket 202). The portion of the rounded front wall 214 nearest to the patient during imaging procedures may be referred to as the front reference surface. The pitch of central portion 212 is depicted specifically in FIG. 3F and may help further conform the paddle 201 to the shape of the breast.

The generally concave surface 206 may also help to prevent the breast from slipping and moving during positioning of the breast, as well as during image acquisition. As an example, this configuration may help prevent slipping of the breast in the MLO position by supporting the breast more, in comparison to known flat compression paddles that often allow the breast to slip during image acquisition. The generally concave surface 206 may have a smooth curvature or can have any other shape that is generally concave, e.g., the surface 206 may include ridges, lines, and/or other elements from injection molding the compression paddle 201, the surface may have a generally trapezoidal shape, etc. Additionally or alternatively, the compression paddle 201 can be used to compress a patient's breast with or without an inflatable jacket and/or a gel pad. In another example, the generally concave surface 206 may not be uniformly concave from the front wall 214 (i.e., the chest facing wall) to the rear edge 216. As compressed breast tissue may not extend as far back as the rear edge 216, the concavity may be greater near the front wall 214 compared to the rear edge 216. As an example, the bottom wall 204 may be generally concave near the front wall 214 and may be flatter near the rear edge 216. In an additional or alternative example, the radius of the generally concave surface 206 is greater near the front wall 214 compared to the bottom wall 204 near the rear edge 216. This non-uniformity may help to provide more even compression from the nipple to the chest wall of the breast.

Generally, the compression paddles of the present technology described herein may be more comfortable to a patient undergoing breast compression during a mammogram or other x-ray imaging of the breast, as well as provide greater technician access to the breast for proper patient positioning. Positioning of the breast is important to produce images that are be diagnostically useful for radiologists. The compression paddles of the present technology described herein generally require less compression force to be applied to accomplish the same tautness as that of a known flat compression paddle. The paddles may be manufactured of substantially rigid or flexible materials. Use of rigid materials allows the paddle to sufficiently compress the breast without undesirably deforming. For example, a distance between the central portion 212 and the plane P may be substantially the same when the paddle 200 is compressing a breast or not compressing a breast. For example, the concave contour of the concave surface 206 may be substantially the same. The particular shapes and contours disclosed herein may reduce or eliminate discomfort during breast compression, and allow for increased access to the breast, as described further below.

The two rounded side walls 208 transition to a curved top surface 218 of the compression paddle 201, although in certain examples, a curved top surface 218 is not utilized and the paddle may be substantially bowl- or plate-shaped, with upper edges of the front wall 219 and rounded side walls 208 terminating at a location proximate where the top surface 218 is depicted. Notably, proximate the rear edge 216 of the compression paddle 201, the bottom wall 204 and rounded side walls 208 transition into access surfaces 220. The access surfaces 220 define an absence of each of the bottom wall 204 and rounded side walls 208. This absence allows for improved access of the technician to the patient breast, for example, when the compression paddle 201 is disposed proximate the breast, or once compression of the breast has begun. The transitions between various adjacent surfaces of the compression paddle 201 are smooth so as to limit patient discomfort and reduce stress locations in the compression paddle 201.

Two additional reference planes are also depicted in FIGS. 3C, 3D, 3E, 3F, and 3H, for clarity. These include a vertical reference plane V and a horizontal reference plane H. Both the vertical reference plane V and the horizontal reference plane H pass through a midpoint M on the curved front wall 214 of the compression paddle 201. The midpoint M is disposed along the axis A of the compression paddle 201, which is defined by the intersection of the vertical reference plane V and the horizontal reference plane H. The compression paddle 201 is symmetrical on either side of the vertical reference plane V. When utilized in an imaging system, the vertical reference plane V is disposed at an angle substantially orthogonal to the breast platform (not shown), while the horizontal reference plane H is disposed substantially parallel to the breast platform.

The complex contours of the compression paddle 201 enable it to comfortably compress the breast, while still allowing technician access to the breast during compression procedures. This allows the technician to manipulate or position the breast as required or desired. During a compression procedure, as well as during subsequent imaging, the front wall 214 is adjacent to and faces a chest wall of a patient. The portion of the front wall 214 closest to the patient chest wall is referred to as a front reference surface.

A plane substantially tangential to this front reference surface is referred to as a front reference plane R and is substantially orthogonal to each of vertical reference plane V, horizontal reference plane H, and bottom reference plane B. The front wall 214 includes a curved lower interface that interfaces with the bottom wall 204. This curved lower interface has an upper extent, e.g., the highest location of the curved lower interface above the bottom reference plane P, the curved surfaces of which increase comfort to the patient during compression. The front reference surface is disposed tangential to this upper extent to further increase comfort. The two outer edge portions 210 define the bottom reference plane P. The bottom wall 204 extends away from the chest wall and is adjacent to a length of a top surface of the compressed breast. As described above, the bottom wall 204 is not flat, but instead includes a central portion 206 that is non-coplanar with the two outer edge portions 210. As depicted in FIG. 3F, a height of the central portion 206 over the bottom reference plane P decreases as a distance away from the front wall 214 increases patient comfort. The edge portions 210 extend away from the front reference plane R and front wall 214. The contours of the compression paddle 201 may also be defined relative to a number of reference planes depicted and described herein. For example, the vertical reference plane V is substantially orthogonal to each of the front reference plane R and the bottom reference plane P. The compression paddle 201 includes a plurality of access surfaces 220 that allow a technician to have improved access to the breast during compression procedures. The shapes, sizes, and configurations of prior art compression paddles often limit technician access to the breast. At best, this would cause improper positioning of the breast during compression, requiring removal of the compression force, attempted repositioning of the breast, and recompression. This can greatly increase procedure time as well as patient anxiety and discomfort. At worst, the technician's hand would get stuck between the breast and the compression paddle. The incorporation of one or more access surfaces 220 on either side of the compression paddle 201 reduces or entirely obviates these problems. The access surfaces 220 are disposed proximate the two outer edge portions 210, namely the curved portions distal the front wall 214, and are defined by a substantially or entirely flat access reference surface. The configuration of the access surfaces 220 is such that they are disposed at non-orthogonal angles to each of the front reference plane R, the bottom reference plane P, and the vertical paddle plane V.

As apparent from FIGS. 3-3H, the compression paddle 201 described herein defines a changing cross section as distance from the front wall 214 increases. These changing cross-sections are further depicted in FIGS. 4A-4E, which depict cross sections of the compression paddle 201 as distance from the front wall 214 increases. The locations of the particular cross sections are depicted in FIG. 3E. In each of FIGS. 4A-4E, the vertical reference plane V, the horizontal reference plane H, and the bottom reference plane P are also depicted. The midpoint M of the front wall 214 is also depicted, and is positioned at the intersection of the vertical reference plane V and the horizontal reference plane H. This intersection also defines the axis A of the compression paddle 201. During use, both the horizontal reference plane H and the bottom reference plane P are disposed a predetermined distance above, and substantially parallel to, a breast compression platform. Vertical reference plane V is substantially orthogonal to the vertical reference plane V, the horizontal reference plane H, the breast platform, and each of the depicted cross sections. Further, the horizontal reference plane H is also orthogonal to each of the depicted cross sections. Each cross section is substantially parallel to the front reference plane R.

FIG. 4A depicts a cross section of the compression paddle 201 at a location proximate the front wall, more particularly, where the front wall 314 transitions to the top surface 218 and bottom wall 204. This cross section is defined by the top wall 218, bottom wall 204, and rounded side walls 208. The cross section defines a first shape that is substantially curved or bean-shaped. The central portion 212 is disposed a distance d above the bottom reference plane P. Each cross section is substantially parallel to the front reference plane R.

With each successive cross section depicted in FIGS. 4B-4E, the cross-sectional shape of the compression paddle 201 changes. As the cross section approaches the bracket end 216 of the compression paddle 201, the changes become more marked. For example, as can be seen, the distance d decreases as the distance away from the front wall 214 (as depicted in FIGS. 4B-4E) increases. Further, the curved shape originally depicted in the cross section of FIG. 4A is altered. Notably, in FIGS. 4D and 4E, the rounded outer ends of this curved shape flattens, as the cross section defines the access corners 220. In the above description, the cross section of the compression paddle 201 is defined by the entire outer surface of the compression paddle 201. However, in other examples, the cross section may only be defined by a portion of the outer surface of the paddle 201. For example, the cross section may be defined by the horizontal reference plane H and the surfaces disposed below that horizontal reference plane H. One reason for such a definition is that the top surface 218 of the compression paddle 201 is largely unchanged at each cross section. Another reason for such a definition is that a top surface 218 is not necessarily always present on every compression paddle. Indeed, the depicted figures depict so-called "hollow" compression paddles that have a hollow interior closed by an outer surface, including the top surface 218. In other examples, the complex bottom shapes of the paddles depicted and described herein (including but not limited to the access surfaces 220) may be utilized on any type of compression paddle. For example, existing compression paddles that utilize an "open" top (i.e., a paddle that does not include a top surface) may also benefit from the complex bottom paddle shapes described herein.

Again with reference to FIGS. 4A-4E, the shape of the compression paddle 201 may be defined based on the outer contours or the cross section of the compression paddle 201 itself. The compression paddle 201 has a front wall that is adjacent to the chest wall of the patient when during imaging procedures. The horizontal reference plane H is disposed at a midpoint M of the front wall (both in horizontal and vertical directions). The bottom wall 204 is configured to be adjacent to the breast of the patient during imaging procedures. The compression paddle 201 may be defined by multiple cross sections. a front cross section (e.g., a cross section closest to the front wall of the compression paddle 201) may be different than a rear cross section. The rear cross section may be disposed a predetermined distance from the front wall, for example, at the end of the compression paddle 201 proximate the bracket.

One aspect of the cross sections that may define the differences therebetween is the position of the bottom wall 204 relative to the bottom reference plane P. Proximate the front wall, the cross section has a central portion 212 intersecting the vertical reference plane P that is disposed a first predetermined distance below the horizontal reference plane H. At the rear cross section, a portion of the bottom wall 204 intersecting the vertical reference plane P is disposed a second predetermined distance below the horizontal reference plane H. In an example where the bottom surface 204 is pitched, the first distance is less than the second distance.

Figure 4E:
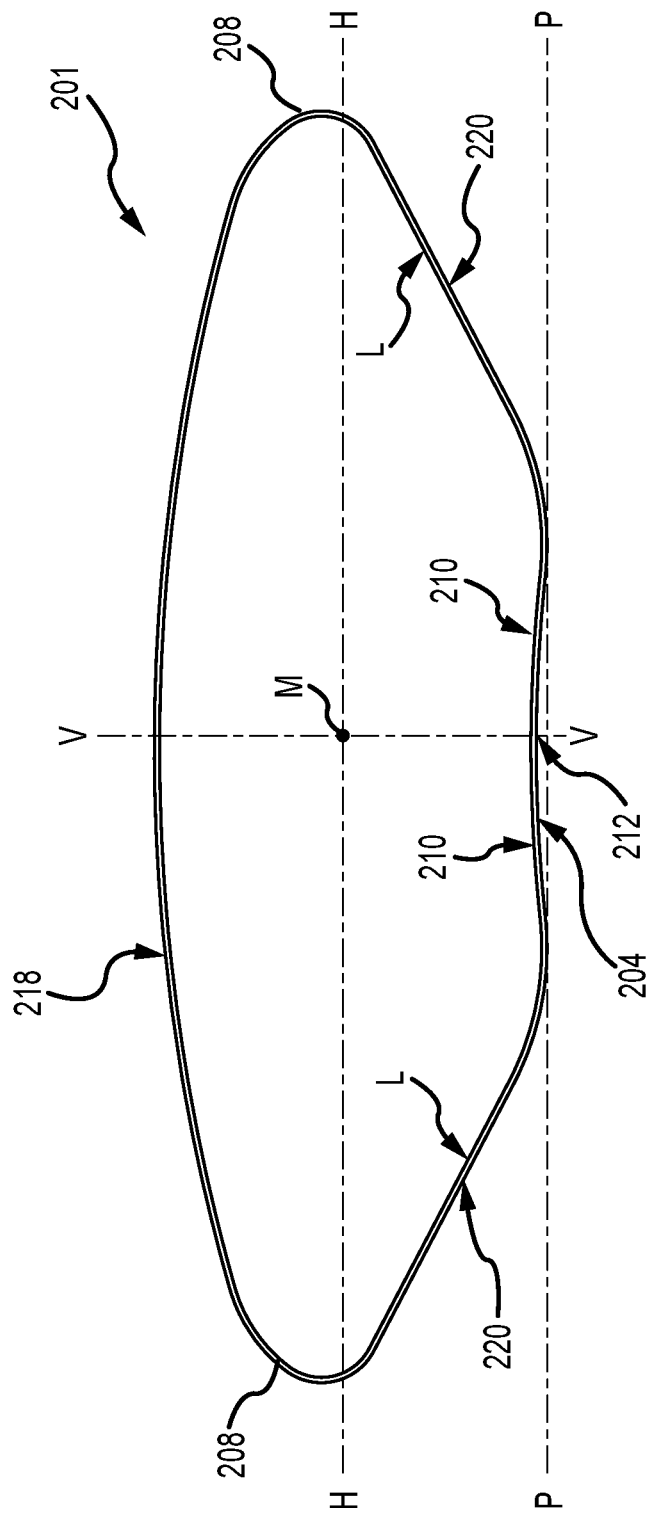

Another aspect of the cross sections that may define the differences therebetween is the configuration of the outer edge portions 210. The two outer edge portions at least partially define the bottom wall 204 and, in the first cross section, are disposed a first distance from the vertical reference plane V. At the second cross section, the two outer edge portions 210 are disposed a second distance from the vertical reference plane V. In such an example, the first distance is greater than the second distance. As the cross sections change in shape from the first cross section to the second cross section and beyond, the outer edge portions 210 include a substantially linear portion (at the first cross section) and a substantially curved portion (at the second cross section). These correspond to the linear and curved portions of the outer edge portions depicted in FIG. 3H. Additionally, FIGS. 4A-4E depict additional differences between the cross sections that may be defined by the outer contours of the compression paddle 201 boundary that defines the cross section. For example, the first cross section includes outer contours defined by a first boundary which may have a first curvature C1 (as depicted in FIG. 4A), while the second cross section includes outer contours defined by a second boundary different than the first boundary. In FIG. 4E, this second boundary is defined by a line which may be substantially straight or have a slight curvature different than that first curvature C1.

The complex shape of the compression paddle 201 may be further defined by the shape of the bottom wall 204. For example, the bottom wall 204 may include a generally concave contact surface 206 that is adjacent to the breast of the patient during imaging procedures. An outer extent of the contact surface 206 may be defined at least in part by two outer edge portions 210. The position of the outer edge portions 210 may vary in each cross section, such as those depicted in FIGS. 4A-4E. As depicted, a distance between the vertical reference plane V and the two outer edge portions 210 decreases as a distance from the front wall 214 increases. Additionally, a distance of the contact surface 206 below the horizontal reference plane H increases as the distance from the front wall 214 increases. As depicted in FIGS. 4A-4E, the plurality of cross sections include outer contours that change in shape as the distance from the front wall 214 increases. For example, the outer contours change from a curved shape defined by curvature C1 (as depicted in FIG. 4A) to a substantially linear shape defined by line L (as depicted in FIG. 4E) as the from the front wall 214 increases. Due to the configuration of the outer edge portions 210, a width of the contact surface 206 changes (e.g., narrows or decreases) as the distance from the front wall 214 increases.

Certain features of the hollow compression paddle depicted in FIGS. 3-4E may also be incorporated into paddles that lack the top surface of the above compression paddle. Such compression paddles, for example, are depicted in FIGS. 10A-12E and 14A-15C of U.S. Pat. No. 9,782,135, the disclosure of which is hereby incorporated by reference herein in its entirety. Such compression paddles generally consist of a single-walled, injection molded element, a bottom surface of which compresses the breast. The sides of that single-walled element are bent or folded upwards so as to form a bowl-like shape, having a front wall connecting two lateral walls. A rear wall of the bowl-like shape is proximate a bracket with which the compression paddle is connected to a compression system of an x-ray imaging system. Thus, the single-walled element has a bottom compression surface; the top surface of that element generally forms the bottom of a bowl-like structure of the compression paddle. Such paddles may have a flat, concave, or convex surface across a whole or a part of the bowl-like structure.

The technologies disclosed herein may improve the usability of these bowl-like compression paddles, e.g., by raising the bracket portion thereof relative to the compression portion to give a technologist improved access to a breast during positioning and compression. This improved access is the result of the compression paddle including a bottom wall having a patient contact surface and a patient access surface. During a compression of the breast, the patient contact surface is in contact with the breast. The patient access surface, however, is disposed a distance above the patient contact surface so as to not contact the breast and provide access to the breast by a technologist. A transition wall having a generally smooth curvature is between and connects the patient contact surface and the patient access surface. In addition to eliminating sharp contact points, the generally smooth curvature of the transition wall may also reduce artifacts that may be formed by the compression paddle during imaging. A front wall of the compression paddle is configured to be in contact with a chest wall during compression. An interface wall is between and connects the patient contact surface and the front wall. Like the transition wall, the interface wall is a generally smooth curvature to reduce or eliminate pressure or pinch points, as well as artifacts.

Although x-ray translucent materials are utilized for the compression paddles described herein, image artifacts may still be formed under certain circumstances. Vertical surfaces may generate artifacts in an image because of the increased amount of material through which the x-ray radiation must pass. As such, in the following examples, vertical surfaces such as the front wall and lateral side walls are disposed outside of an imaging area to prevent generation of such artifacts. Sharp transitions from one surface to another (e.g., corners or intersecting edges) may also form image artifacts for similar reasons. As such, the compression paddles described below utilize smooth contours on all surfaces in the imaging area so as to reduce or prevent such artifacts.

The compression paddles described below incorporate additional features so as to improve manufacturability and conformance with the compression paddle with the breast. These include the use of ribs or other structures below a bracket portion of a compression paddle to increase rigidity thereof. The ribs also allow the compression paddle to be formed in a single injection molding process. The use of the smooth contours described above also reduces stress points in the paddle, while allowing the compression portion of the paddle to better conform to the shape of the breast. The compression portion of the paddle also lacks the above-described ribs, which allows the compression portion to deflect during breast compression. These smooth shapes and deflection capability helps reduce discomfort commonly associated with flat paddles.

Figure 5A:
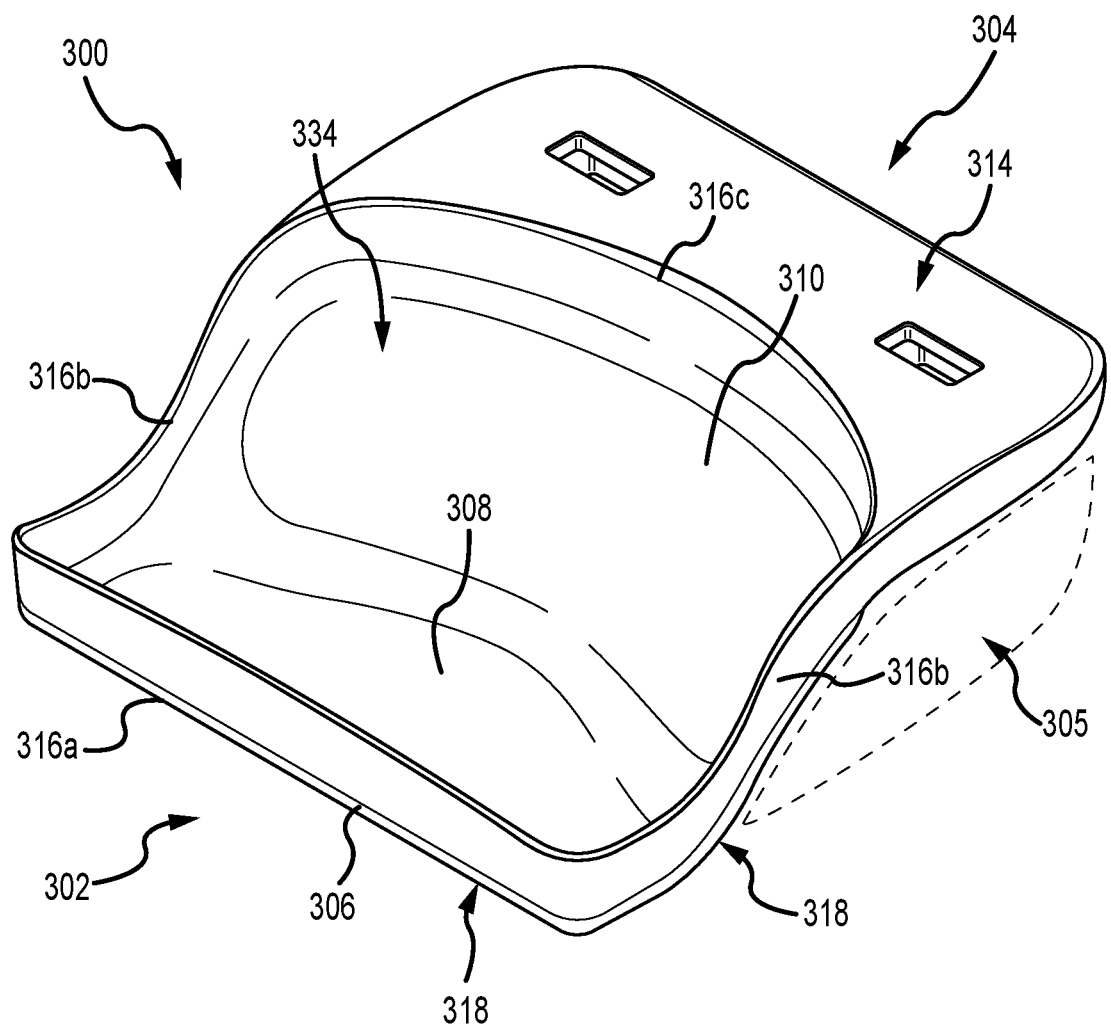
Figure 5B:
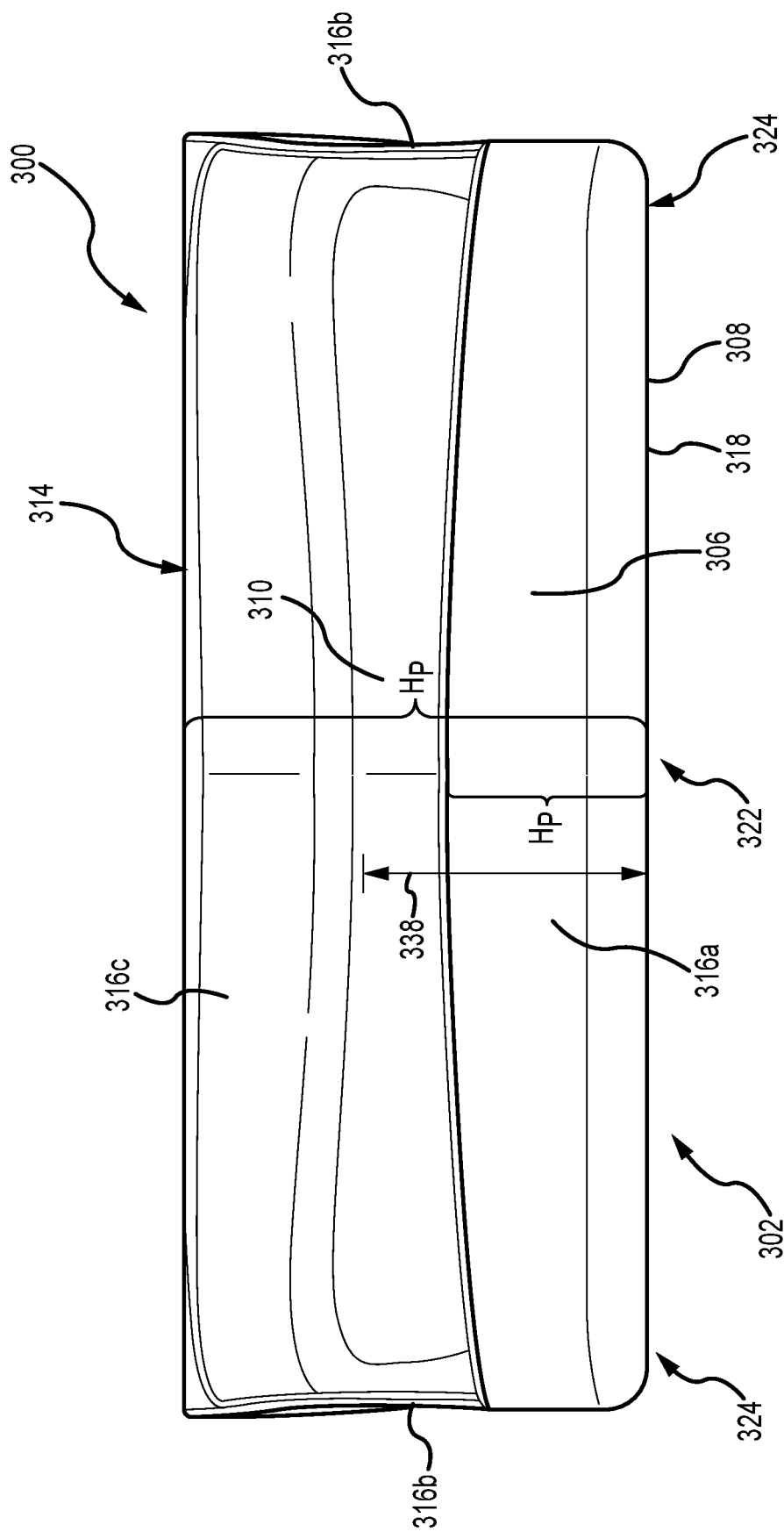

FIGS. 5A-5C are perspective, front, and side views, respectively, of an example of a bowl-like compression paddle 300, and are described concurrently. The compression paddle includes a compression portion 302 and a bracket portion 304. The compression portion 302 is configured to be disposed proximate the chest wall of a patient during compression, while the bracket portion 304 is used to secure the compression paddle 300 to a compression arm of an imaging system. The bracket portion 304 is raised relative to the compression portion 302 so as to define an access area 305 below at least a portion of the compression paddle 300, which allows a technologist to better access a patient breast during positioning. The access area 305 is depicted generally by dashed lines in FIGS. 5A and 5C. Of course, the compression paddle 300 is a three-dimensional object, as such, the so called "access area" is actually a volume primarily disclosed below the bracket portion 304 and an angled wall (in this case, transition wall 310) of the compression paddle 300. A front wall 306 is disposed so as to contact the chest wall of a patient. A bottom wall 308 acts as a compression surface for the breast during imaging procedures. The transition wall 310 extends towards the bracket portion 304 and at least partially defines the access area 305. A rear bracket wall 312 extends down from a surface 314 that defines the top-most extent of both the bracket portion 304 and the compression paddle 300 as a whole. A plurality of ribs 315 extend from the rear bracket wall 312 so as to provide structural rigidity to the compression paddle 300; more specifically, the ribs 315 provide structural rigidity to the bracket portion 304. The configuration of the compression portion 302, that is, of an open, bowl-like structure, allows for flexure of the compression portion 302 during compression of the breast. A boundary wall 316 generally defines the open, bowl-like structure. The boundary wall 316 includes a front boundary wall 316a, lateral boundary walls 316b, and a rear boundary wall 316c. The front boundary wall 316a is generally coextensive with the front wall 306.

As noted above, the front wall 306 is configured to be adjacent to and face a chest wall of a patient during imaging. The front wall 306 includes a front wall height H, a curved lower interface 318 that connects to the bottom wall 308, and a front reference plane 320. The bottom wall 308 extends away from the chest wall and, during imaging, is adjacent a length of a top of a compressed breast. The bottom wall 308 includes a generally central portion 322 and two outer edge portions 324 that at least partially define the central portion 322. The two outer edge portions 324 extend away from the front reference plane 320, for example, as depicted most clearly in the side view of FIG. 5C. The generally central portion 322 extends away from the front reference plane 320 a greater distance than the two outer edge portions 324. As such, the shape of the bottom wall 308 general corresponds to the outer shape of the compressed breast. The two outer edge portions 324 (or at least three points disposed thereon) define a bottom reference plane 326 that is substantially orthogonal to the front reference plane 320. The bottom reference plane 326, in this case, is generally a horizontal plane that is substantially consistent with the bottom surface of the paddle 300. The bracket portion 304 is distal from the front wall 306, and includes the paddle top surface 314 and a bracket underside surface 328. The paddle top surface 314 defines a top reference plane 330 that is substantially parallel to the bottom reference plane 326. The top reference plane 330 is disposed a maximum paddle height $H_P$ above the bottom reference plane 326. This maximum paddle height $H_P$ is greater than the front wall height H, which again helps improve technologist access to the breast.

The rear bracket wall 312 is disposed opposite the front wall 306 and connects the paddle top surface 314 and the bracket underside surface 328, and wherein the rear bracket wall terminates at a distance 332 above the bottom reference plane 326 that is greater than the front wall height H. In examples, such as that depicted in FIGS. 5A-5C, the bracket underside surface 328 is defined as a portion of the paddle 300 that is disposed directly below the flat paddle top surface 314 that defines the top reference plane 326. In examples, the lowermost portion of each of the plurality of ribs 315 (again, below the flat paddle top surface 314) act as the bracket underside surface 328. The angled transition wall 310 connects the bracket underside surface 328 and the bottom wall 308. Thus, the bracket portion 304 of the compression paddle 300 is considerably higher than the compression portion 302, allowing a technologist to have improved access to the breast during positioning and compression.

When the compression paddle 300 is viewed from above, for example, from the perspective of FIG. 5A, the bottom wall 308 and the transition wall 310 are substantially surrounded by the boundary or perimeter wall 316 that extends upward towards the top reference plane 330. Thus, viewed from this perspective, the bottom wall 308, the transition wall 310, and the boundary or perimeter wall 316 define a semi-bounded volume 334. In the depicted example, the bottom wall 308 and the transition wall 310 form a lower surface of the semi-bounded volume 334 where the bottom wall 308 is non-concave. More specifically, the bottom wall 308 is substantially flat. The transition wall 310 is substantially convex when viewed from above. The two lateral boundary walls 316b extend from the front boundary wall 316a to the rear boundary wall 316c, and slope generally upward along the transition wall 310. The bottom wall 308 is connected to each of the boundary walls 316 at a curved interface 318. As described above, an uppermost portion of the front boundary wall 316a has a front boundary wall height H above the bottom reference plane 326. An uppermost portion of the rear boundary wall 316c is connected to and approximately the same height as that of the top surface 314 of the bracket portion 304. Thus, this rear boundary wall height above the bottom reference plane 326, is generally the same as the maximum paddle height $H_P$, such that the front boundary wall height H is less than the rear boundary wall height above the bottom reference plane 326. The two outer edge portions 324 of the bottom wall 308 are disposed proximate the two lateral boundary walls 316b. The bottom wall 308 also includes a proximate portion 335 that is disposed proximate the front boundary wall 316a and a distal portion 336 disposed distal from the front boundary wall 316a which in this example is generally level with the proximate portion 336. As depicted in FIG. 5C, a high portion 337 of the transition wall 310 is disposed a high portion distance 338 above the bottom reference plane 326. In the compression paddle 300 of FIG. 5A-5C, the high portion distance 338 is greater than the front boundary wall height H. As can be seem most clearly in FIG. 5A, the rear boundary wall 316c is generally curved along its length and is closest to the rear paddle wall 312 proximate a mid-point of that curvature. The ribs 315 can be seen as extending from the rear boundary wall 316c to the rear paddle wall 312.

Figure 6A:
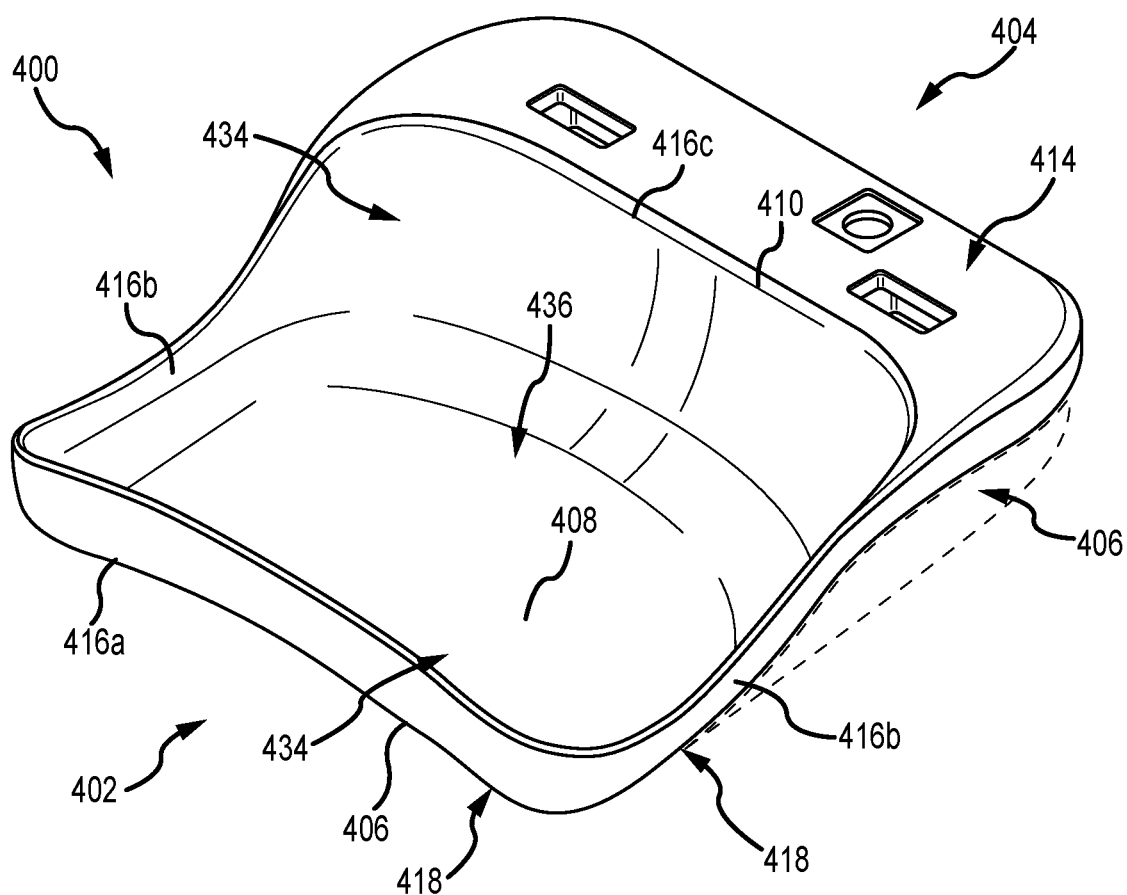

FIGS. 6A-6C are perspective, front, and side views, respectively, of another example of a compression paddle 400, and are described concurrently. The compression paddle includes a compression portion 402 and a bracket portion 404. The compression portion 402 is configured to be disposed proximate the chest wall of a patient during compression, while the bracket portion 404 is used to secure the compression paddle 400 to a compression arm of an imaging system. The bracket portion 404 is raised relative to the compression portion 402 so as to define an access area 406 below at least a portion of the compression paddle 400, which allows a technologist to better access a patient breast during positioning, as described above. A front wall 406 is disposed so as to contact the chest wall of a patient. A bottom wall 408 acts as a compression surface for the breast during imaging procedures. A transition wall 410 extends towards the bracket end 404 and at least partially defines the access area 406. A rear bracket wall 412 extends down from a surface 414 that defines the top-most extent of both the bracket portion 404 and the compression paddle 400. A plurality of ribs 415 extend from the rear bracket wall 412 so as to provide structural rigidity to the compression paddle 400, namely to the bracket portion 404. The open, bowl-like configuration of the compression end 402 allows for flexure of the compression portion 402 during compression of the breast. A boundary wall 416 generally defines the open, bowl-like structure. The boundary wall 416 includes a front boundary wall 416a, lateral boundary walls 416b, and a rear boundary wall 416c. The front boundary wall 416a is generally coextensive with the front wall 406.

As noted above, the front wall 406 is configured to be adjacent to and face a chest wall of a patient during imaging. The front wall 406 includes a front wall height H, a curved lower interface 418 that connects to the bottom wall 408, and a front reference plane 420. The bottom wall 408 extends away from the chest wall and, during imaging, is adjacent a length of a top of a compressed breast. The bottom wall 408 includes a generally central portion 422 and two outer edge portions 424 that at least partially define the central portion 422. In this example, the generally central portion 422 is raised relative to the two outer edge portions 424, which extend away from the front reference surface 420, for example, as depicted most clearly in the side view of FIG. 6C. The two outer edge portions 424 (or at least three points disposed thereon) define the bottom reference plane 426 that is substantially orthogonal to the front reference plane 420. The bottom reference plane 426, in this case, is generally a horizontal plane that is defined by the lowermost points of the paddle 400. The bracket portion 404 is distal from the front wall 406, and includes the paddle top surface 414 and a bracket underside surface 428. The paddle top surface 414 defines a top reference plane 430 that is substantially parallel to the bottom reference plane 426. The top reference plane 430 is disposed a maximum paddle height $H_P$ above the bottom reference plane 426. This maximum paddle height $H_P$ is greater than the front wall height H, thus improving technologist access.

The rear bracket wall 412 is disposed opposite the front wall 406 and connects the paddle top surface 414 and the bracket underside surface 428, and wherein the rear bracket wall 412 terminates at a distance 432 above the bottom reference plane 426 that is greater than the front wall height H. In examples, such as that depicted in FIGS. 6A-6C, the bracket underside surface 428 is defined as a portion of the paddle 400 that is disposed directly below the flat paddle top surface 414 that defines the top reference plane 426. In examples, the lowermost portion of each of the plurality of ribs 415 (again, below the flat paddle top surface 414) act as the bracket underside surface 428. In this example, the ribs 415 extend to a location on the angled transition wall 410 that is lower than the front wall height H. The angled transition wall 410 connects the bracket underside surface 428 and the bottom wall 408. The bracket portion 404 of the compression paddle 400 is considerably higher than the compression portion 402, allowing a technologist to have improved access to the breast during positioning and compression.

When the compression paddle 400 is viewed from above, for example, from the perspective of FIG. 6A, the bottom wall 408 and the transition wall 410 are substantially surrounded by the boundary or perimeter wall 416 that extends upward towards the top reference plane 430. Thus, viewed from this perspective, the bottom wall 408, the transition wall 410, and the boundary or perimeter wall 416 define a semi-bounded volume 434. In the depicted example, the bottom wall 408 and the transition wall 410 form a lower surface of the semi-bounded volume 434 where the bottom wall 408 is non-concave. More specifically, the bottom wall 408 is convex, as depicted in FIG. 6B. The transition wall 410 is substantially concave when viewed from above. The two lateral boundary walls 416b extend from the front boundary wall 416a to the rear boundary wall 416c, and slope generally upward along the transition wall 410. The bottom wall 408 is connected to each of the boundary walls 416 at a curved interface 418. As described above, an uppermost portion of the front boundary wall 416a has a front boundary wall height H above the bottom reference plane 426. An uppermost portion of the rear boundary wall 416c is connected to and approximately the same height as that of the top surface 414 of the bracket portion 404. Thus, this rear boundary wall height above the bottom reference plane 426, is generally the same as the maximum paddle height $H_P$, such that the front boundary wall height H is less than the rear boundary wall height above the bottom reference plane 426. The two outer edge portions 424 of the bottom wall 408 are disposed proximate the two lateral boundary walls 416b. The bottom wall 408 also includes a proximate portion 434 that is disposed proximate the front boundary wall 416a and a distal portion 436 disposed distal from the front boundary wall 416a. The distal portion 436 is proximate the transition wall 410 and is disposed a distance d above the bottom reference plane 426. This distance d allows the compression portion 402 to flex upward without contacting a breast support platform disposed beneath. As depicted in FIG. 6C, a high portion 437 of the transition wall 410 is disposed a high portion distance 438 above the bottom reference plane 426. In the compression paddle 400 of FIG. 6A-6C, the high portion distance 438 is greater than the front boundary wall height H. As can be seem most clearly in FIG. 6A, the rear boundary wall 416c is generally parallel the rear paddle wall 412. The ribs 415 can be seen as extending from the rear boundary wall 416c to the rear paddle wall 412.

Figure 7A:
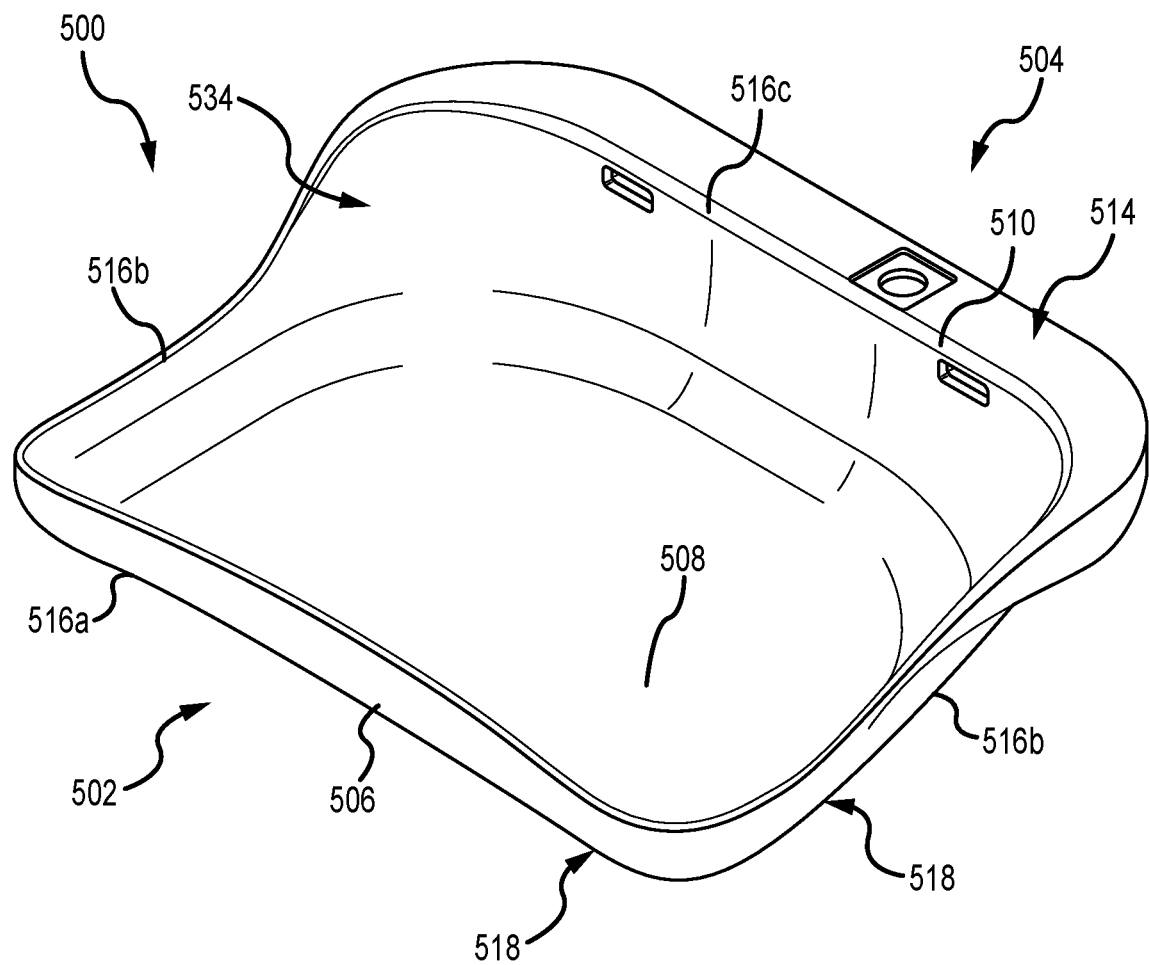
Figure 7B:
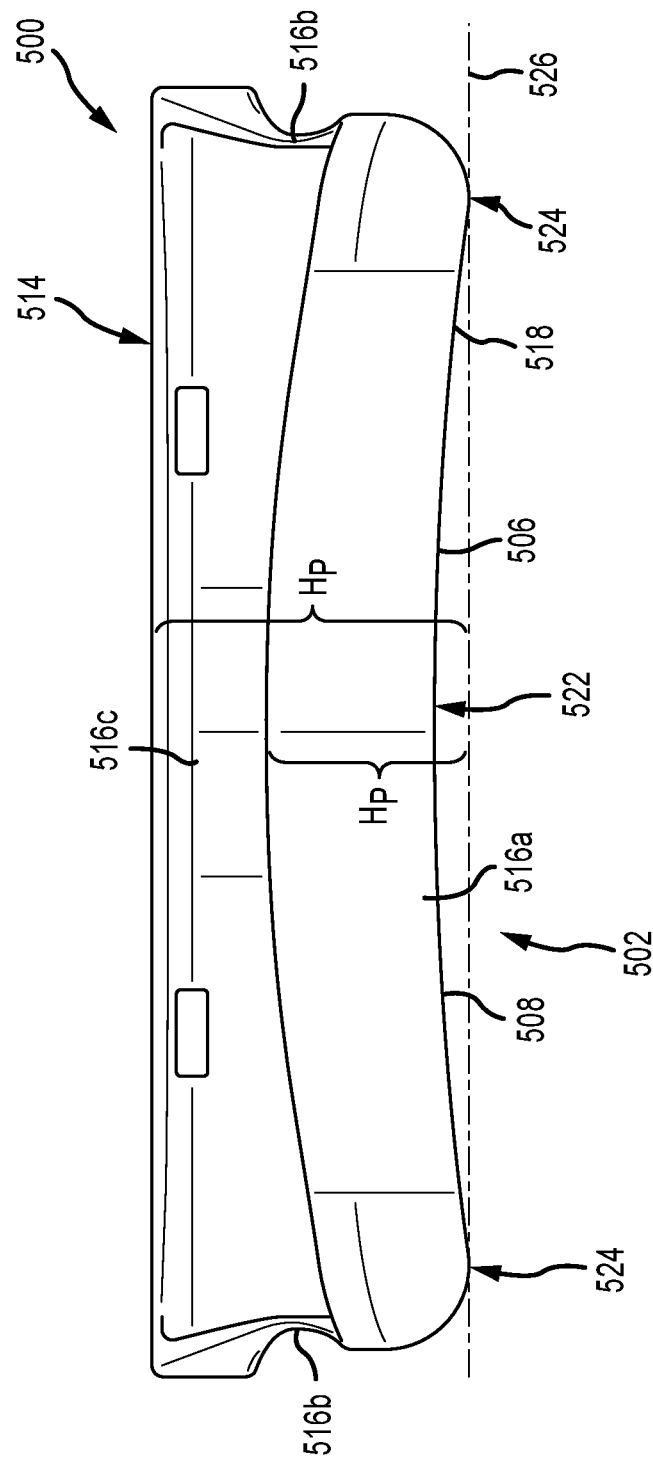

FIGS. 7A-7C are perspective, front, and side views, respectively, of another example of a compression paddle 500, and are described concurrently. The compression paddle includes a compression portion 502 and a bracket portion 504. The compression portion 502 is configured to be disposed proximate the chest wall of a patient during compression, while the bracket portion 504 is used to secure the compression paddle 500 to a compression arm of an imaging system. The bracket portion 504 is raised relative to the compression portion 502 so as to define an access area 506 below at least a portion of the compression paddle 500, which allows a technologist to better access a patient breast during positioning, as described above. A front wall 506 is disposed so as to contact the chest wall of a patient. A bottom wall 508 acts as a compression surface for the breast during imaging procedures. A transition wall 510 extends towards the bracket portion 504 and at least partially defines the access area 506. A rear bracket wall 512 extends down from a surface 514 that defines the top-most extent of both the bracket portion 504 and the compression paddle 500. A plurality of ribs 515 extend from the rear bracket wall 512 so as to provide structural rigidity to the compression paddle 500, namely to the bracket portion 504. The open, bowl-like configuration of the compression portion 502 allows for flexure of the compression portion 502 during compression of the breast. A boundary wall 516 generally defines the open, bowl-like structure. The boundary wall 516 includes a front boundary wall 516a, lateral boundary walls 516b, and a rear boundary wall 517O. The front boundary wall 516a is generally coextensive with the front wall 506.

As noted above, the front wall 506 is configured to be adjacent to and face a chest wall of a patient during imaging. The front wall 506 includes a front wall height H, a curved lower interface 518 that connects to the bottom wall 508, and a front reference plane 520. The bottom wall 508 extends away from the chest wall and, during imaging, is adjacent a length of a top of a compressed breast. The bottom wall 508 includes a generally central portion 522 and two outer edge portions 524 that at least partially define the central portion 522. In this example, the generally central portion 522 is raised relative to the two outer edge portions 524, which extend away from the front reference surface 520, for example, as depicted most clearly in the side view of FIG. 7C. The two outer edge portions 524 (or at least three points disposed thereon) define the bottom reference plane 526 that is substantially orthogonal to the front reference plane 520. The bottom reference plane 526, in this case, is generally a horizontal plane that is defined by the lowermost points of the paddle 500. The bracket portion 504 is distal from the front wall 506, and includes the paddle top surface 514 and a bracket underside surface 528. The paddle top surface 514 defines a top reference plane 530 that is substantially parallel to the bottom reference plane 526. The top reference plane 530 is disposed a maximum paddle height $H_P$ above the bottom reference plane 526. This maximum paddle height $H_P$ is greater than the front wall height H, thereby improving technologist access.

The rear bracket wall 512 is disposed opposite the front wall 506 and connects the paddle top surface 514 and the bracket underside surface 528, and wherein the rear bracket wall 512 terminates at a distance 532 above the bottom reference plane 526 that is greater than the front wall height H. In examples, such as that depicted in FIGS. 7A-7C, the bracket underside surface 528 is defined as a portion of the paddle 500 that is disposed directly below the flat paddle top surface 514 that defines the top reference plane 526. In examples, the lowermost portion of each of the plurality of ribs 515 (again, below the flat paddle top surface 514) act as the bracket underside surface 528. In this example, the ribs 515 extend to a location on the angled transition wall 510 that is lower than the front wall height H. The angled transition wall 510 connects the bracket underside surface 528 and the bottom wall 508. The bracket portion 504 of the compression paddle 500 is considerably higher than the compression portion 502, allowing a technologist to have improved access to the breast during positioning and compression.

When the compression paddle 500 is viewed from above, for example, from the perspective of FIG. 7A, the bottom wall 508 and the transition wall 510 are substantially surrounded by the boundary or perimeter wall 516 that extends upward towards the top reference plane 530. Thus, viewed from this perspective, the bottom wall 508, the transition wall 510, and the boundary or perimeter wall 516 define a semi-bounded volume 534. In the depicted example, the bottom wall 508 and the transition wall 510 form a lower surface of the semi-bounded volume 534 where the bottom wall 508 is non-concave. More specifically, the bottom wall 508 is convex, as depicted in FIG. 7B. The transition wall 510 is substantially concave when viewed from above. The two lateral boundary walls 516b extend from the front boundary wall 516a to the rear boundary wall 517C, and slope generally upward along the transition wall 510. The bottom wall 508 is connected to each of the boundary walls 516 at a curved interface 518. As described above, an uppermost portion of the front boundary wall 516a has a front boundary wall height H above the bottom reference plane 526. An uppermost portion of the rear boundary wall 516C is connected to and approximately the same height as that of the top surface 514 of the bracket portion 504. Thus, this rear boundary wall height above the bottom reference plane 526, is generally the same as the maximum paddle height $H_P$, such that the front boundary wall height H is less than the rear boundary wall height above the bottom reference plane 526. The two outer edge portions 524 of the bottom wall 508 are disposed proximate the two lateral boundary walls 516b. The bottom wall 508 also includes a proximate portion 534 that is disposed proximate the front boundary wall 516a and a distal portion 536 disposed distal from the front boundary wall 516a. The distal portion 536 is proximate transition wall 510 and is disposed a distance d above the bottom reference plate 526. This distance d allows the compression portion 502 to flex upwards without contacting a breast support platform disposed beneath. As depicted in FIG. 7C, a high portion 537 of the transition wall 510 is disposed a high portion distance 538 above the bottom reference plane 526. In the compression paddle 500 of FIG. 7A-7C, the high portion distance 538 is greater than the front boundary wall height H. As can be seem most clearly in FIG. 7A, the rear boundary wall 517C is generally parallel the rear paddle wall 512. The ribs 515 can be seen as extending from the rear boundary wall 516C to the rear paddle wall 512.

Figure 8:
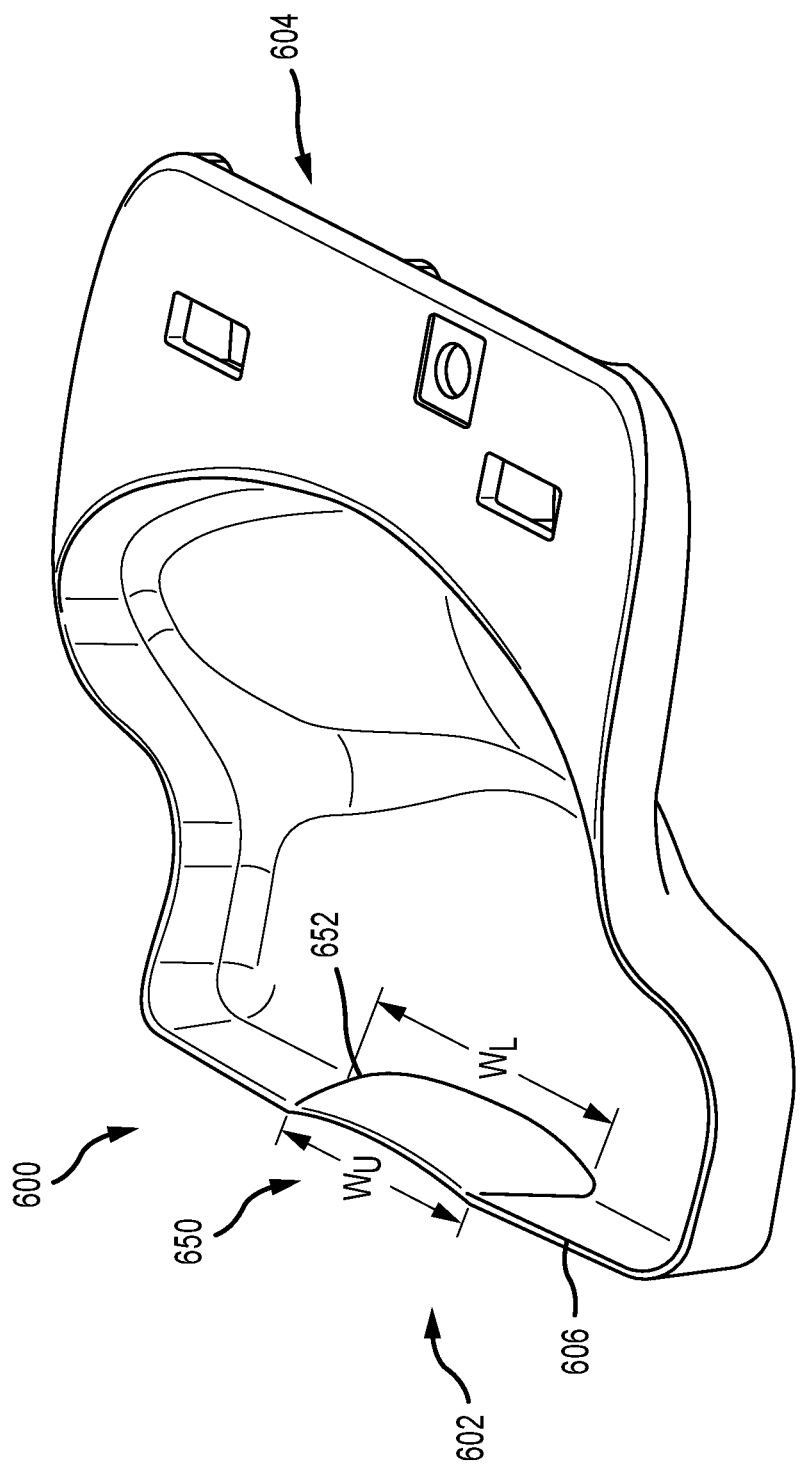
FIG. 8 is a rear perspective view of another example of a compression paddle.

FIG. 8 is a rear perspective view of another example of a compression paddle 600. The compression paddle 600 includes a compression end 602 and a bracket end 604 and is generally configured consistent with the compression paddle 300 of FIGS. 5A-5C. However, the compression paddles 400, 500 depicted in FIGS. 6A-7C may be similarly modified to include such a recess. In this example, the front wall 606 at least partially defines a recess or indentation 650. The recess 650 is defined by an upper width $W_U$ and a lower width $W_L$ that is wider than the upper width $W_U$. The recess 650 includes a curved wall 652 that is further disposed at an angle to that of the front wall 606. This recess 650 is particularly advantageous for obtaining unobstructed views of breasts that include silicone or saline breast implants. The curved wall 652 of the recess 650 is focused to the focal source of the imaging system. The curved wall 652 of the recess 650 pushes the implant out of the compression area below the paddle 600. In examples, the upper width $W_U$ may be about 50 percent of the lower width $W_L$. In other examples, the upper width $W_U$ may be between about 45-60 percent, between about 40-70 percent, or between about 35-80 percent of the lower width $W_L$.

Figure 9A:
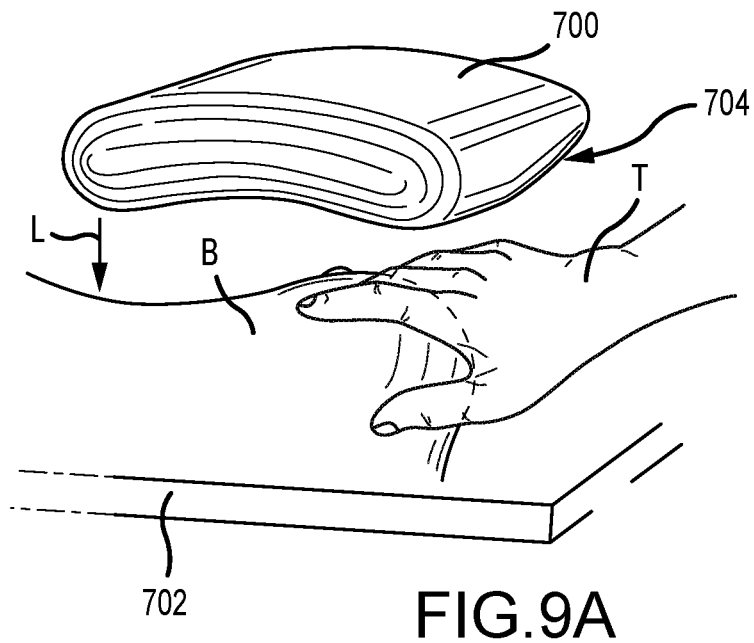
FIGS. 9A-9C depict a method of using a compression paddle.
Figure 9B:
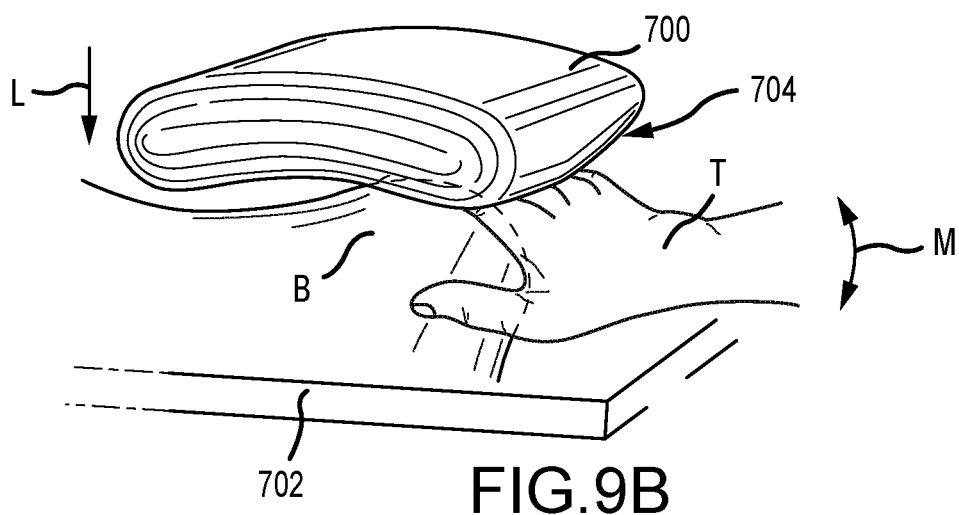
Figure 9C:
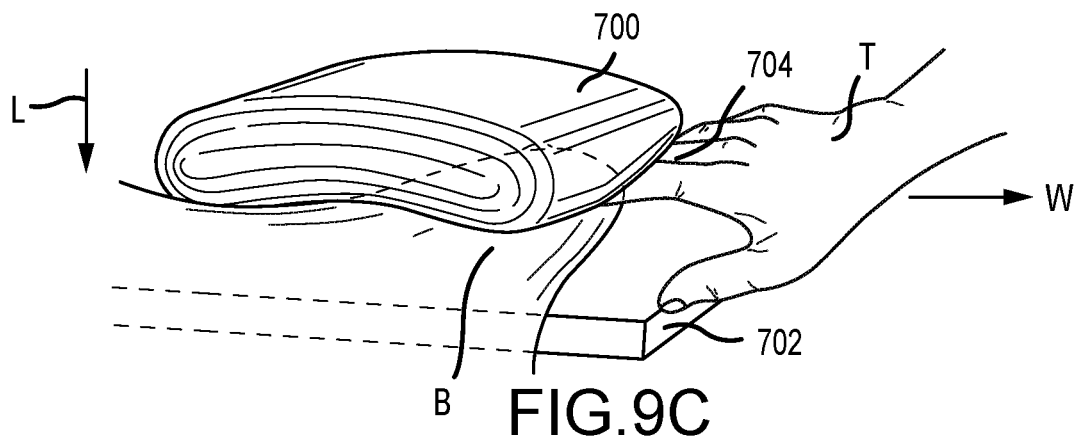

FIGS. 9A-9C depict a method of using a compression paddle 700 prior to an imaging procedure. In the depicted figures, the torso of the patient is not depicted, for clarity. Additionally, a compression paddle 700 similar to that depicted in FIGS. 3-4E is depicted. The other paddles depicted above in FIGS. 5A-8 may also be utilized with similar results, due to the access areas located below the paddle brackets, as described above. In FIGS. 9A-9C, an approximate location of the breast B and technician T manipulating the breast B on a platform 702 is depicted. Once the breast is placed on the platform 702, it is held in place by the technician T as the compression paddle 700 is lowered L, as depicted in FIG. 9A. FIG. 9B depicts the condition where the compression paddle 700 first contacts the breast B. The technician T may move M her hand so as to position the breast B as required. With prior art compression paddles, this position, with the compression paddle in initial contact with the breast, may begin to cause interference between the technician and the compression paddle. The access corners 704 of the present compression paddle 700, however, allow the technician T to move her hand relative to the breast B, with minimal, if any, interference with the compression paddle 700. In FIG. 9C, the compression paddle 700 is further lowered L, leading to further compression. Due to the configuration of the compression paddle 700, namely the access corners 704, the technician T may manipulate and position the breast B for longer without fear of her hand being caught between the compression paddle 700 and the breast B. Thus, the technician T is able to maintain contact with the breast B for longer, prior to withdrawing W her hand and beginning imaging procedures.

This disclosure described some examples of the present technology with reference to the accompanying drawings, in which only some of the possible examples were shown. Other aspects can, however, be embodied in many different forms and should not be construed as limited to the examples set forth herein. Rather, these examples were provided so that this disclosure was thorough and complete and fully conveyed the scope of the possible examples to those skilled in the art.

Although specific examples were described herein, the scope of the technology is not limited to those specific examples. One skilled in the art will recognize other examples or improvements that are within the scope of the present technology. Therefore, the specific structure, acts, or media are disclosed only as illustrative examples. Examples according to the invention may also combine elements or components of those that are disclosed in general but not expressly exemplified in combination, unless otherwise stated herein. The scope of the technology is defined by the following claims and any equivalents therein.

The invention claimed is:

1. A breast compression paddle comprising:
   a compression portion having:
      a front wall configured to be adjacent to and to face towards a chest wall of a patient during imaging, wherein the front wall comprises a front wall height, a curved lower interface, and a front reference plane adjacent the chest wall, the front reference plane being substantially along a vertical direction of the breast compression paddle; and
      a bottom wall connected to the curved lower interface and configured to extend away from the chest wall and to be adjacent a length of a top of a compressed breast, wherein the bottom wall comprises a central portion and two outer edge portions at least partially defining the central portion, wherein the two outer edge portions extend away from the front reference plane, wherein the two outer edge portions are a lowermost portion of the breast compression paddle and define a bottom reference plane substantially orthogonal to the front reference plane, and wherein the front wall height is defined between the bottom reference plane and an uppermost portion of the front wall in the vertical direction;
   a bracket portion distal from the compression portion, wherein the bracket portion comprises a paddle top surface, a bracket underside surface, and a rear boundary wall, the paddle top surface extending from the rear boundary wall in a direction away from the compression portion. and wherein the paddle top surface comprises a top reference plane disposed a maximum paddle height above the bottom reference plane, and wherein the maximum paddle height is greater than the front wall height; and
   a transition wall extending between the bottom wall and the bracket underside surface, wherein an access area is at least partially defined between the bottom reference plane, the transition wall, and the bracket underside surface, and wherein the rear boundary wall is disposed above the access area.

2. The breast compression paddle of claim 1, wherein the bracket portion comprises a rear bracket wall disposed opposite the front wall and connecting the paddle top surface and the bracket underside surface, and wherein the rear bracket wall terminates at a distance above the bottom reference plane greater than the front wall height.

3. The breast compression paddle of claim 1, wherein the bracket underside surface comprises a portion of the breast compression paddle disposed directly below the paddle top surface that defines the top reference plane.

4. The breast compression paddle of claim 1, further comprising a plurality of ribs disposed below the paddle top surface.

5. The breast compression paddle of claim 1, wherein the bottom wall and the transition wall are substantially surrounded by a perimeter wall extending upward towards the top reference plane. the perimeter wall including the rear boundary wall, wherein the bottom wall, the transition wall, and the perimeter wall define a semi-bounded volume.

6. The breast compression paddle of claim 5, wherein the bottom wall and the transition wall comprise a lower surface of the semi-bounded volume, and wherein a portion of the lower surface proximate the bottom wall is non-concave.

7. The breast compression paddle of claim 6, wherein a portion of the lower surface proximate the transition wall is substantially concave.

8. The breast compression paddle of claim 6, wherein a portion of the lower surface proximate the transition wall is substantially convex.

9. The breast compression paddle of claim 1, wherein the front wall comprises an indentation disposed at an angle to the front wall.

10. A breast compression paddle comprising:
    a plurality of boundary walls extending substantially along a vertical direction of the breast compression paddle, the plurality of boundary walls comprising a front boundary wall, a rear boundary wall, and two lateral boundary walls extending from the front boundary wall to the rear boundary wall;
    a bracket portion extending from the rear boundary wall away from the front boundary wall; and
    a bottom wall connected to each of the plurality of boundary walls at a curved interface, wherein the bottom wall comprises a proximate portion disposed proximate to the front boundary wall, the bottom wall at the proximate portion comprises at least three lowermost points relative to the vertical direction and defining a bottom reference plane substantially orthogonal to the vertical direction, wherein the bottom wall further comprises a distal portion disposed distal from the front boundary wall, the distal portion is disposed a distal portion distance above the bottom reference plane, an access area is at least partially defined between the bottom reference plane and the distal portion, and wherein the rear boundary wall is disposed above the access area, and wherein an uppermost portion of the front boundary wall is disposed at a front boundary wall height above the bottom reference plane, and wherein an uppermost portion of the rear boundary wall is disposed at a rear boundary wall height above the bottom reference plane, and wherein the front boundary wall height is less than the rear boundary wall height.

11. The breast compression paddle of claim 10, wherein the bottom wall comprises a raised central portion and a plurality of outer edge portions, and wherein the at least three points are disposed on the plurality of outer edge portions.

12. The breast compression paddle of claim 10, wherein the bottom wall comprises two outer edge portions disposed proximate the two lateral boundary walls, and a central portion substantially level with the two outer edge portions.

13. The breast compression paddle of claim 10, wherein the bracket portion is connected to the rear boundary wall and comprises a rear paddle wall disposed opposite from the rear boundary wall and disposed substantially parallel to the rear boundary wall.

14. The breast compression paddle of claim 13, further comprising a plurality of ribs spanning from the rear boundary wall to the rear paddle wall.

15. The breast compression paddle of claim 14, wherein at least one of the plurality of ribs contacts at least a portion of the bottom wall.

16. The breast compression paddle of claim 10, wherein at least a portion of the distal portion of the bottom wall is convex.

17. The breast compression paddle of claim 10, wherein the front boundary wall defines a recess having an upper width disposed proximate the uppermost portion of the front boundary wall and a lower width disposed proximate the bottom wall, wherein the lower width is greater than the upper width.

18. The breast compression paddle of claim 17, wherein the recess is disposed at an angle to the front boundary wall.

19. A breast compression paddle comprising:

a bottom wall having a patient contact surface and a patient access surface, wherein during a compression of a breast, the patient contact surface is in contact with the breast and the patient access surface is disposed a distance from the patient contact surface so as to not contact the breast, wherein the bottom wall extends substantially horizontally relative to a vertical direction, and wherein at least three lowermost points of the bottom wall relative to the vertical direction define a bottom reference plane;

a transition wall between and connecting the patient contact surface and the patient access surface, wherein the transition wall has a generally smoothly curved shape that rises upwardly from the bottom reference plane from the patient contact surface towards the patient access surface such that the patent access surface is positioned above the patient contact surface relative to the vertical direction, an access area is at least partially defined between the bottom reference plane, the transition wall, and the patient access surface;

a plurality of boundary walls extending from the bottom wall, the plurality of boundary walls comprising a front wall extending from the patient contact surface and an opposite rear wall extending from the transition wall, wherein during the compression of the breast, the front wall is in contact with a chest wall, and wherein the rear wall is disposed above the access area; and an interface wall between and connecting the patient contact surface and the front wall, wherein the interface wall has a generally smoothly curved shape.

* * * * *